US011610676B2

(12) United States Patent
Matsumoto et al.

(10) Patent No.: US 11,610,676 B2
(45) Date of Patent: Mar. 21, 2023

(54) INFORMATION PROCESSING DEVICE AND INFORMATION PROCESSING METHOD

(71) Applicant: KONICA MINOLTA, INC., Tokyo (JP)

(72) Inventors: Hiroaki Matsumoto, Yokohama (JP); Hitoshi Futamura, Hachioji (JP); Satoshi Kasai, Hachioji (JP); Shinsuke Katsuhara, Kodaira (JP); Tsuyoshi Kobayashi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 1140 days.

(21) Appl. No.: 16/212,650

(22) Filed: Dec. 6, 2018

(65) Prior Publication Data

US 2019/0189278 A1    Jun. 20, 2019

(30) Foreign Application Priority Data

Dec. 15, 2017    (JP) .............................. JP2017-240131

(51) Int. Cl.
*G06F 3/048*    (2013.01)
*G16H 50/20*    (2018.01)
(Continued)

(52) U.S. Cl.
CPC ............. *G16H 50/20* (2018.01); *G06N 20/00* (2019.01); *G16H 30/40* (2018.01)

(58) Field of Classification Search
CPC ......... G16H 50/20; G16H 30/40; G06N 20/00
See application file for complete search history.

(56) References Cited

U.S. PATENT DOCUMENTS

2005/0010445 A1*   1/2005   Krishnan ............... G16H 50/20
                                                                706/45
2005/0102315 A1*   5/2005   Krishnan .............. G06T 7/0012
                                                              707/999.102
(Continued)

FOREIGN PATENT DOCUMENTS

JP    2009034517 A       2/2009
JP    2011239797 A  *  12/2011   ........... G06T 7/0012
(Continued)

OTHER PUBLICATIONS

Japanese Office Action (and English language translation thereof) dated May 25, 2021 issued in Japanese Application No. 2017-240131.

(Continued)

*Primary Examiner* — Rashawn N Tillery
(74) *Attorney, Agent, or Firm* — Holtz, Holtz & Volek PC

(57) ABSTRACT

An information processing device includes: a plurality of identifiers that discriminates whether abnormal data that is information indicating an abnormal value is included in treatment data and detects the abnormal data; and a hardware processor that: customizes evaluation data used when evaluating discrimination accuracy of the plurality of identifiers; calculates the discrimination accuracy of each of the plurality of identifiers using the evaluation data customized by the hardware processor; and selects one identifier out of the plurality of identifiers as an identifier used for discrimination based on a calculation result by the hardware processor.

8 Claims, 12 Drawing Sheets

(51) Int. Cl.
     *G06N 20/00*     (2019.01)
     *G16H 30/40*     (2018.01)

(56) References Cited

U.S. PATENT DOCUMENTS

| | | | |
|---|---|---|---|
| 2009/0034810 A1* | 2/2009 | Oakley | G06T 7/0012 |
| | | | 382/128 |
| 2009/0097730 A1* | 4/2009 | Kasai | A61B 6/502 |
| | | | 382/132 |
| 2013/0044927 A1* | 2/2013 | Poole | G06T 7/0014 |
| | | | 382/128 |
| 2017/0011186 A1* | 1/2017 | Oosawa | G06F 16/00 |
| 2019/0197368 A1* | 6/2019 | Madani | G06N 3/082 |
| 2019/0348161 A1* | 11/2019 | Liang | G16H 50/70 |

FOREIGN PATENT DOCUMENTS

| | | | | |
|---|---|---|---|---|
| JP | 2011239797 A | | 12/2011 | |
| JP | 5533662 B2 | | 6/2014 | |
| JP | 2015191287 A | | 11/2015 | |
| JP | 2019158684 A | * | 9/2019 | |
| WO | 2010050334 A1 | | 5/2010 | |
| WO | WO-2010050334 A1 | * | 5/2010 | A61B 6/563 |

OTHER PUBLICATIONS

Inenaga, et al., "Support Vector Machine (SVM)", Sep. 10, 2004, vol. 104 No. 318.
Suzuki, et al., "Deep Convolutional Neural Network", Jun. 16, 2015.

\* cited by examiner

| IDENTIFIER | ABNORMAL SHADOW DETECTION | NORMAL IMAGE ERRONEOUS DETECTION |
|---|---|---|
| IDENTIFIER A | 90% | 5% |
| IDENTIFIER B | 85% | 5% |
| ⋮ | ⋮ | ⋮ |

FIG. 9

| IDENTIFIER | EVALUATION CHARACTERISTIC | ABNORMAL SHADOW DETECTION | NORMAL IMAGE ERRONEOUS DETECTION |
|---|---|---|---|
| IDENTIFIER A | DISCRIMINATION ACCURACY USING EVALUATION DATA OF FACILITY A | 90% | 5% |
| | DISCRIMINATION ACCURACY USING EVALUATION DATA OF FACILITY B | 80% | 5% |
| | DISCRIMINATION ACCURACY USING EVALUATION DATA OF ELDERLY PATIENTS | 99% | 5% |
| | DISCRIMINATION ACCURACY USING EVALUATION DATA OF OUTPATIENTS | 95% | 5% |
| IDENTIFIER B | DISCRIMINATION ACCURACY USING EVALUATION DATA OF FACILITY A | 85% | 5% |
| | DISCRIMINATION ACCURACY USING EVALUATION DATA OF FACILITY B | 95% | 5% |
| | DISCRIMINATION ACCURACY USING EVALUATION DATA OF ELDERLY PATIENTS | 75% | 5% |
| | DISCRIMINATION ACCURACY USING EVALUATION DATA OF OUTPATIENTS | 85% | 5% |
| ⋮ | DISCRIMINATION ACCURACY USING EVALUATION DATA OF FACILITY A | ⋮ | ⋮ |
| | DISCRIMINATION ACCURACY USING EVALUATION DATA OF FACILITY B | ⋮ | ⋮ |
| | DISCRIMINATION ACCURACY USING EVALUATION DATA OF ELDERLY PATIENTS | ⋮ | ⋮ |
| | DISCRIMINATION ACCURACY USING EVALUATION DATA OF OUTPATIENTS | ⋮ | ⋮ |

INFORMATION PROCESSING DEVICE AND INFORMATION PROCESSING METHOD

The entire disclosure of Japanese patent Application No. 2017-240131, filed on Dec. 15, 2017, is incorporated herein by reference in its entirety.

BACKGROUND

Technological Field

The present invention relates to an information processing device and an information processing method.

Description of the Related Art

In a medical field, treatment is performed such that a doctor checks treatment data (medical information) obtained by various kinds of examinations and reads presence or absence of various abnormalities from an examination result.

For example, in a case where the treatment data is a medical image, the medical image generated in a modality such as a computed radiography (CR) device, a flat panel detector (FPD) device, a computed tomography (CT) device, and a magnetic resonance imaging (MRI) device is displayed on a display unit (monitor), and interpretation diagnosis is performed in which the doctor observes a state of a lesion site and change with time.

However, it takes a lot of labor for the doctor to check all the treatment data from the first. For this reason, various diagnosis assist systems are devised in order to assist the doctor in diagnosing.

For example, JP 2011-239797 A proposes an image diagnosis assist device which detects an abnormal shadow suspected to be a lesion from a medical image when treatment data is the medical image.

In addition, JP 5533662 B2 proposes an information processing device which forms an identifier by learning using learning data and automatically checks treatment data with this identifier as a method of assisting a doctor in diagnosing.

JP 5533662 B2 discloses that, in a case where there is a plurality of identifiers, discrimination accuracy of each of them is calculated using evaluation data, and an identifier most excellent in discrimination accuracy is applied.

In this manner, by forming the information processing device for assisting the doctor in diagnosing by applying the identifier excellent in discrimination accuracy, it is possible to make a check result of the treatment data performed automatically by the device more reliable.

However, the treatment data obtained in medical institutions have different characteristics for each medical institution. For example, in a medical institution in which most of patients are elderly patients and a medical institution in which most of patients are young such as children, types of diseases suffered by the patients also differ, and the characteristics of the treatment data also significantly differ.

Therefore, in a case where the evaluation data used for evaluating discrimination accuracy of the identifier is the evaluation data not reflecting the characteristics and the like of the users of the medical institution in which the identifier is used, there is a case where the discrimination accuracy calculated by using the evaluation data does not match the characteristic and trend of the medical institution, and the identifier evaluated to have the highest discrimination accuracy is not optimal for individual medical institution.

SUMMARY

The present invention is achieved in view of the above circumstances, and an object thereof is to provide an information processing device and an information processing method capable of appropriately evaluating discrimination accuracy of an identifier for discriminating presence or absence of abnormal data.

To achieve the abovementioned object, according to an aspect of the present invention, an information processing device reflecting one aspect of the present invention comprises: a plurality of identifiers that discriminates whether abnormal data that is information indicating an abnormal value is included in treatment data and detects the abnormal data; and a hardware processor that: customizes evaluation data used when evaluating discrimination accuracy of the plurality of identifiers; calculates the discrimination accuracy of each of the plurality of identifiers using the evaluation data customized by the hardware processor; and selects one identifier out of the plurality of identifiers as an identifier used for discrimination based on a calculation result by the hardware processor.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 9 is a view illustrating an example of an evaluation result in the third embodiment;

DETAILED DESCRIPTION OF EMBODIMENTS

Hereinafter, one or more embodiments of the present invention will be described with reference to the drawings.

Although various technically preferable limitations are given to the embodiments described below in order to implement the present invention, the technical scope of the present invention is not limited to the following embodiments and illustrated examples.

First Embodiment

First, with reference to FIGS. 1 to 5, a first embodiment of an information processing device and an information processing method according to the present invention are described.

The information processing device according to this embodiment is provided in a medical image system to process treatment data (treatment information and medical information including medical image data and the like) obtained by various types of modalities.

[Regarding Medical Image System]

Figure 1:
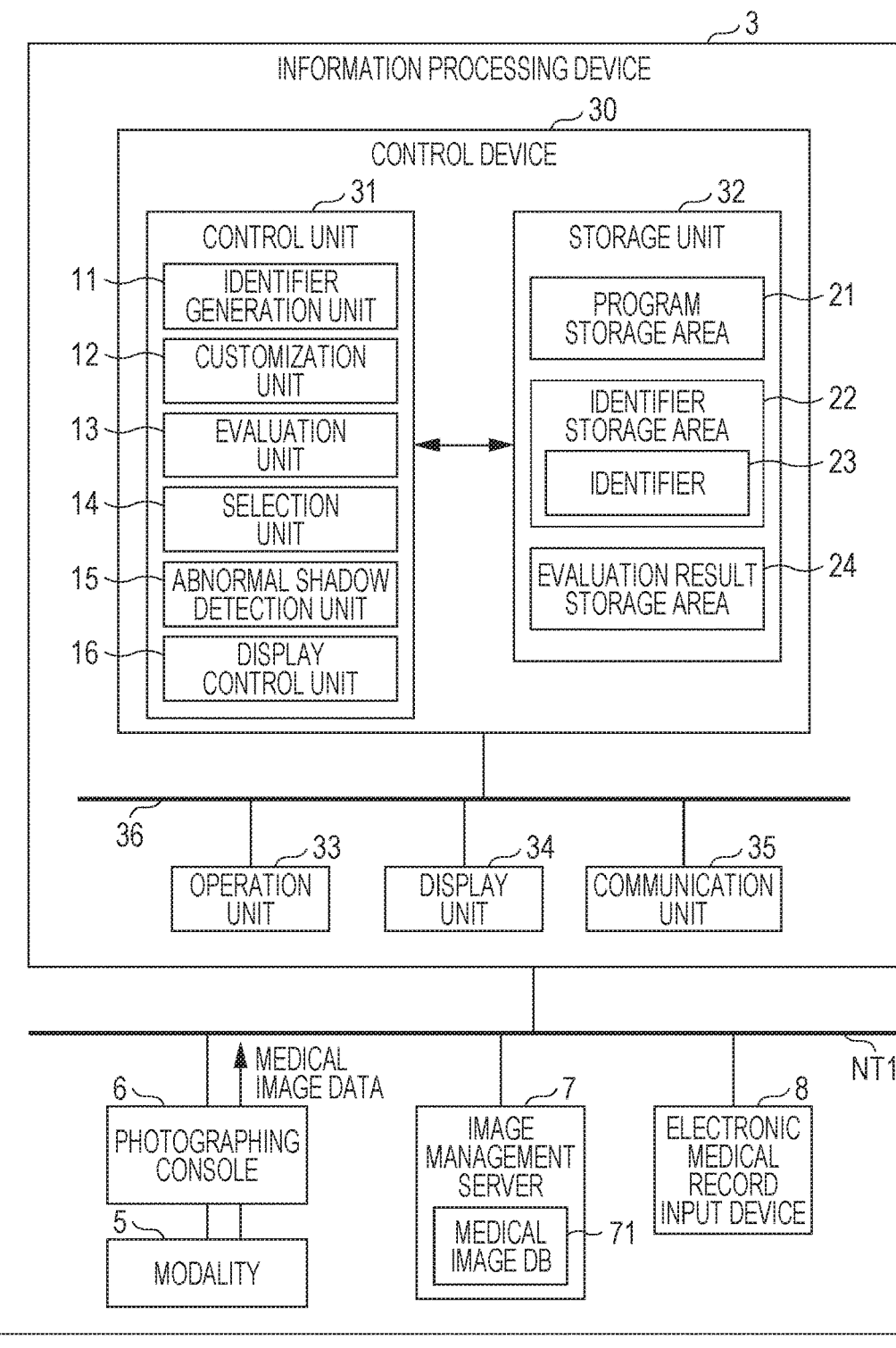
FIG. 1 is a configuration diagram of a substantial part illustrating a system configuration of a medical image system including an information processing device according to a first embodiment.

FIG. 1 is a configuration diagram of a substantial part illustrating a system configuration of the medical image system provided with the information processing device according to this embodiment.

As illustrated in FIG. 1, a medical image system 100 provided in a facility H ("facility A Ha" in FIG. 1) which is a medical institution performs examination photographing of a patient to generate and manage the medical image data and the like as the treatment data.

In this embodiment, as the facility H which is the medical institution, a general hospital, a doctor's office where a general practitioner is practicing individually, a relatively small-scale medical facility such as a clinic, a medical office and the like are assumed.

Meanwhile, the facility H which is the medical institution may be any facility in which medical images and the like as the medical information are handled, and is not limited to those herein illustrated.

The medical image system 100 is provided with various types of modalities (image generation devices) 5 which generate the medical image, a photographing console 6 which controls photographing operation by the modality 5, an image management server 7 provided with a medical image data base (DB) 71 which stores and manages data of the medical image obtained by the modality 5 (medical image data) and the like, an electronic medical record input device 8, and an information processing device 3 which discriminates whether the medical image includes abnormal data. The photographing console 6 connected to the modality 5, the image management server 7, the electronic medical record input device 8, and the information processing device 3 are connected to a network NT1 via a switching hub and the like not illustrated, and may transmit/receive data via the network Nil.

Each device connected via the network Nil and forms the medical image system 100 is in conformity to, for example, the Digital Image and Communications in Medicine (DICOM) standards being communication standards to handle medical-related data in general, and communication between the devices is performed according to the DICOM. Meanwhile, the number of the devices is not especially limited.

In addition, elements forming the medical image system 100 are not limited to those herein illustrated, and another storage unit, server and the like may also be included.

Also, it is not indispensable that the medical image system 100 is provided with the image management server 7 and the electronic medical record input device 8. For example, the image management server 7 and the like may be provided outside the medical image system 100 and configured to be able to transmit and receive the data via an external network not illustrated.

The modality 5 provided in the medical image system 100 photographs a site to be examined of a patient, performs digital conversion on the photographed image, and generates the medical image data and the like as the medical information.

As the modality 5, for example, a CR (computed radiography, plain radiography) device, a flat panel detector (FPD) device, a mammography device, a computed tomography (CT) device, an ultrasonic diagnostic device, an endoscope device and the like are assumed, but this is not limited to them.

Meanwhile, only one set of the modality 5 and the photographing console 6 is illustrated in FIG. 1, but a plurality of modalities 5 and the like may be provided in the medical image system 100. In this case, a plurality of modalities 5 of the same type may be provided, or a plurality of modalities 5 of different types may be provided.

When each device forming the medical image system 100 is in conformity to the DICOM standards, the image data of the medical image (medical image data) is stored in a DICOM file format according to the DICOM standards. The DICOM file is formed of an image part and a header. Actual data of the medical image is written in the image part, and accompanying information regarding the medical image is written in the header. Meanwhile, in this embodiment, the medical image data and the information accompanying the same (accompanying information and additional information) are also collectively referred to as the "treatment data".

The accompanying information includes, for example, patient information, examination information, and image detailed information.

Herein, the patient information includes various pieces of information regarding the patient of the medical image such as patient identification information (for example, a patient ID) for identifying the patient, a patient's name, sex, birth date and the like.

Also, the examination information includes various pieces of information and the like regarding examination such as examination identification information (for example, an examination ID) for identifying the examination, examination date, the type of modality, an examination site, and a doctor in charge.

The image detailed information includes various pieces of information regarding the medical image such as an image ID, image generation time, and a file path name indicating a storage location of the medical image.

The medical image data obtained by the modality 5 is transmitted to the image management server 7 connected to the network NT1 via the photographing console 6 and is stored in the medical image DB 71 and the like together with the accompanying information.

Meanwhile, in a case where the medical image is in a format not compliant with the DICOM, this is preferably stored in the medical image DB and the like after the format thereof is converted to a format compliant with the DICOM, or after a unique ID (UID) for individually specifying the medical image is added to the medical image.

The image management server 7 is a computer device which accumulates, stores, and manages the image data of the medical image (medical image data) generated by the modality 5 and the accompanying information (treatment data being the medical information) regarding the medical image.

Specifically, the image management server 7 includes the medical image DB 71 formed of a hard disk and the like.

As described above, the medical image data stored in the medical image DB 71 is stored in the DICOM file format according to the DICOM standards.

The DICOM file is formed of the image part and the header, and the medical image DB 71 includes a medical image management table for storing the accompanying information of the medical image and stores the medical images in a retrievable manner.

When the medical image is received from the modality 5, the image management server 7 stores the received medical image in the medical image DB 71 and registers the accompanying information thereof in the medical image management table.

Also, the image management server 7 includes a storage unit (electronic medical record information data base (DB)) not illustrated which stores the electronic medical record information input from the electronic medical record input device 8.

In the electronic medical record information DB of the image management server 7, the patient information of each item such as the patient ID, name, sex, age, body weight, body height, body temperature, medical interview result, entry date and the like is stored.

The electronic medical record input device 8 is a device for inputting electronic medical record information such as the patient information and medical interview result.

Information (electronic medical record information) input from the electronic medical record input device 8 is also stored in the medical image DB 71 and the like in association with the medical image data.

Meanwhile, the electronic medical record information may include, for example, the patient information of each item such as the patient ID, name, sex, age, body weight, body height, body temperature, medical interview result, and entry date, but there is no limitation.

[Regarding Information Processing Device]

The information processing device 3 detects whether an abnormal shadow which is the abnormal data is included as for the treatment data including the medical image data which is the medical information, and assists the doctor and the like in diagnosing.

In this embodiment, the information processing device 3 is provided with a control device 30, an operation unit 33, a display unit 34, a communication unit 35 and the like, and the units are connected by a bus 36.

The operation unit 33 is provided with a keyboard including a cursor key, number input keys, various function keys and the like and a pointing device such as a mouse, for example, and outputs an instruction signal input by key operation on the keyboard and mouse operation to the control device 30.

The display unit 34 formed of a monitor such as a liquid crystal display (LCD) and a cathode ray tube (CRT) displays various screens, the medical image and the like according to an instruction of a display signal input from the control device 30.

The communication unit 35 provided with a LAN adapter, a router, a terminal adapter (TA) and the like transmits and receives the data to and from each device connected to the network NT1.

The control device 30 of the information processing device 3 is provided with a control unit 31 formed of a CPU and the like not illustrated, and a storage unit 32 formed of a ROM, a RAM and the like not illustrated.

In the control device 30, the control unit 31 reads out various programs stored in the ROM of the storage unit 32 and develops them in a working area of the RAM, and cooperates with the programs to realize various functions.

In this embodiment, the control unit 31 functionally includes an identifier generation unit 11, a customization unit 12, an evaluation unit 13, a selection unit 14, an abnormal shadow detection unit 15, a display control unit 16 and the like.

The identifier generation unit 11 generates a new identifier 23 by performing machine learning of the identifier 23 stored in the storage unit 32 (an identifier storage area 22 to be described later).

The identifier 23 discriminates whether the abnormal data which is information indicating an abnormal value is included in the medical image included in the treatment data being the medical information and detects the abnormal data.

In this embodiment, the abnormal data is a value indicating the abnormal shadow which is the abnormal data suspected to be a lesion, and the identifier 23 is used for discriminating the presence or absence of this abnormal shadow, and assists the doctor in diagnosing.

In an initial state of the information processing device 3, the identifier 23 is, for example, a general-purpose identifier 23 set at a factory shipping stage.

Meanwhile, the identifier 23 which is already used in the information processing device 3 and the like of another facility H may be mounted in place of the general-purpose identifier 23 in the initial state of the information processing device 3. In this case, by introducing the identifier 23 used in the facility H having a characteristic close to that of the facility H which newly introduces the information processing device 3 (for example, the facility H and the like in which many patients close in generation to the patient expected to use the facility H are treated), it is possible to expect discrimination accuracy matching the characteristic of the relevant facility H to some extent from the initial stage.

The identifier 23 is formed by repeating learning (machine learning) using learning data of initial setting at the time of initial use.

As a method of such machine learning, for example, there are Expectation-Maximization (EM) algorithm and Bayesian learning (for example, variational Bayesian method) as a method of utilizing clustering by mixed distribution in addition to AdaBoost (or AdaBoostMlt which is multi-valued AdaBoost), artificial neural network and support vector machine, there is no limitation.

As the learning data of the initial setting, a large amount of general-purpose data without bias in data trend is used.

The identifier generation unit 11 uses not the learning data of the initial setting but the treatment data including the medical image data collected at the relevant medical institution (facility A Ha in FIG. 1) in which the identifier 23 is used as the learning data, so that it is possible to form a new identifier 23 customized to match the characteristic of the relevant facility H (facility A Ha in FIG. 1) as compared to the existing identifier 23 to allow the identifier 23 to discriminate the abnormal shadow at higher accuracy.

In order to generate the new identifier 23 having different characteristics, the learning data used for learning may be changed to another new data, or the method of machine learning may be changed even if the same learning data is used. For example, even if the learning is performed using the same learning data, different results may be obtained by changing the method of the machine learning from the AdaBoost to the support vector machine or variational Bayesian method, and it is possible to generate the new identifier 23. The new identifier 23 may be generated also by changing a parameter applied in a process of the machine learning.

Meanwhile, information on the presence or absence of abnormality such as the abnormal shadow is associated with the learning data and evaluation data.

The learning of the identifier 23 using the learning data and calculation of the discrimination accuracy of the identifier 23 using the evaluation data are performed on the basis of the information on the presence or absence of various abnormalities associated with the learning data and evaluation data.

That is, the information on the presence or absence of the abnormality associated with each data is correct answer information on whether the learning data and evaluation data include the abnormal data, and if so, which type of abnormal data is included; at the time of learning of the identifier 23 and calculation of the discrimination accuracy of the identifier 23, it is evaluated whether the identifier 23 may correctly discriminate such information.

Meanwhile, the information regarding the presence or absence of the abnormal shadow and the like is associated with corresponding learning data and evaluation data on the basis of a result of image interpretation by a doctor or a result of definite diagnosis when the definite diagnosis is obtained by another examination and the like, for example.

The customization unit 12 is a customizer which customizes the evaluation data used when evaluating the discrimination accuracy of a plurality of identifiers 23.

In this embodiment, as for a plurality of identifiers 23 obtained by learning, the discrimination accuracy thereof is evaluated by using the evaluation data, and the customization unit 12 customizes the evaluation data to be used for evaluation.

Specifically, the customization unit 12 adopts the treatment data including the medical image data which is the medical information collected at the medical institution (facility A Ha in FIG. 1) in which the identifier 23 is used as the evaluation data.

As a result, it is possible to evaluate whether the discrimination accuracy of the identifier 23 may be said to be high accuracy in discrimination matching the characteristic of the medical institution (facility A Ha in FIG. 1).

That is, for example, if the facility A Ha is a hospital with many elderly patients, it is required that the discrimination accuracy of the abnormal shadow regarding diseases by which elder patients are likely to be affected is high. However, the treatment data collected from the facility other than this medical facility includes many treatment data of young patients and pediatric patients, and even if the discrimination accuracy of the abnormal shadow is high for these data, it cannot be said that the discrimination accuracy required for the facility A Ha is satisfied. In this respect, if the treatment data collected at the facility A Ha in which the identifier 23 is used is adopted as the evaluation data, it is possible to appropriately evaluate the discrimination accuracy matching the characteristic of this facility.

Meanwhile, when the number of treatment data collected at the medical institution in which the identifier 23 is used (facility A Ha in FIG. 1) is large, the customization unit 12 may select a part of the treatment data randomly or according to a certain criterion to make the same the evaluation data.

In this case, as for whether to adopt this as the evaluation data, a user operates the operation unit 33 and the like to arbitrarily select from a list to input, and when this selection/input result is output to the control device 30, the customization unit 12 may adopt the treatment data selected by the user as the evaluation data in response to the selection result.

Also, for example, it is also possible to set in advance to adopt the treatment data of elderly patients of a certain age or older as the evaluation data, or set a condition such as a criterion and a threshold to preferentially adopt such that a ratio of the treatment data of the elderly patients of a certain age or older is large, and the customization unit 12 selects the treatment data to be adopted as the evaluation data so as to meet a condition set in advance from the patient information (for example, sex and age) and the like included in the treatment data.

Furthermore, in a case where the doctor's interpretation or another photographing is performed after the abnormal shadow is discriminated by the identifier 23 regarding the medical image (for example, in a case where the medical image on which the discrimination of the abnormal shadow is performed by the identifier 23 is performed is an image of plain radiography using the CR device and three-dimensional photographing by the CT device is performed thereafter), in a case where a correct answer for the image discriminated by the identifier 23 is confirmed by later interpretation or photographing (that is, for the image discriminated to include abnormal shadow in the abnormal shadow discrimination by the identifier 23, in a case where the presence of the abnormal shadow is confirmed by the later interpretation or photographing (when the identifier 23 gets the correct answer), or in a case where it is confirmed that there is no abnormal shadow (when the identifier 23 cannot get the correct answer)), all the treatment data in which the correct answer is fixed may be included in the evaluation data.

Also, the customization unit 12 may adopt the treatment data in which the identifier 23 currently used erroneously discriminates as the evaluation data. This makes it possible to confirm whether the discrimination accuracy is improved so that the data which the identifier 23 erroneously discriminates before is correctly discriminated when the evaluation unit 13 evaluates.

The evaluation unit 13 is an evaluator which calculates the discrimination accuracy of each of a plurality of identifiers 23 by using the evaluation data customized by the customization unit 12. An evaluation result of the discrimination accuracy of each identifier 23 by the evaluation, unit 13 is stored in an evaluation result storage area 24 of the storage unit 32.

Figures 2, 3:
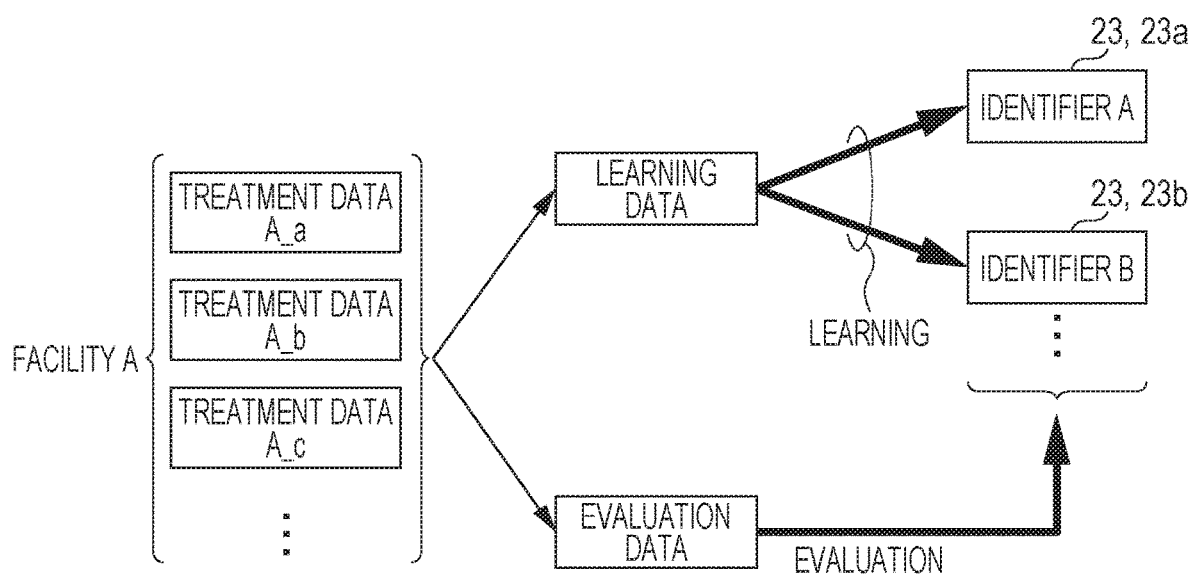
FIG. 2 is an illustrative view schematically illustrating a method of learning and evaluating discrimination accuracy of an identifier in the first embodiment.
FIG. 3 is a view illustrating an example of an evaluation result in the first embodiment.

FIG. 2 is an illustrative view schematically illustrating a method of learning and evaluating the discrimination accuracy of the identifier 23 in this embodiment.

As illustrated in FIG. 2, for example, in a case where the treatment data collected at the facility A Ha are treatment data A_a, treatment data A_b, treatment data A_c and the like, they are divided into the learning data used for the learning of the identifier 23 and the evaluation data used for evaluating the discrimination accuracy, and the learning (machine learning) of the identifier 23 (identifier A23a and identifier B23b in FIG. 2) and the evaluation of the discrimination accuracy are performed by using the respective data.

By making the learning data and the evaluation data different from each other as described above, it is possible to appropriately evaluate whether the abnormal shadow may be correctly discriminated also for new data which is not learned.

Also, since the evaluation data is customized by the customization unit 12 so that the treatment data collected at the facility (facility A Ha in this embodiment) in which the identifier 23 is used is used as the evaluation data, the evaluation unit 13 may appropriately evaluate the discrimination accuracy for the data according to the characteristic at the facility (facility A Ha).

In this embodiment, the evaluation unit 13 evaluates each of the identifiers 23 by using the evaluation data in two viewpoints; a ratio at which the abnormal shadow may be discriminated and a ratio at which a normal image is erroneously recognized as including the abnormal shadow.

FIG. 3 illustrates a calculation result in a case Where the detection ratio of the abnormal shadow and the ratio at which the normal image is erroneously recognized as including the abnormal shadow are calculated for each identifier 23 (identifiers A23a and B23b in FIG. 2).

In the result illustrated in FIG. 3, there is no difference in ratio of erroneously recognizing the normal image between the identifiers A23a and B23b (5%), but as for the detection ratio of the abnormal shadow, this is 90% for the identifier A23a and 85% for the identifier B23b, so that the discrimination accuracy of the identifier A23a is more excellent by 5%.

The selection unit 14 is a selector which selects one identifier 23 out of a plurality of identifiers 23 (identifier A23a and identifier B23b in FIG. 2) as the identifier 23 used to discriminate whether there is the abnormal data (abnormal shadow) on the basis of the calculation result by the evaluation unit 13.

In this embodiment, when the user selects and inputs the identifier 23 which is wanted to be used at the facility H by operating the operation unit 33 and the like based on the calculation result by the evaluation unit 13, and the selection/input result is output to the control device 30, the selection unit 14 selects to set the identifier 23 selected by the user as the one to be used for discriminating the presence or absence of the abnormal data (abnormal shadow) in response to the selection result, That is, in a case where the one other than the identifier 23 currently used at the facility H is selected, the identifier 23 is switched to the selected one.

Specifically, the information processing device 3 of this embodiment is provided with the display unit 34 as a display which displays various pieces of information and images, and the display control unit 16 as a unit of controlling the same, and the display control unit 16 allows the display unit 34 to display information on the discrimination accuracy calculated for a plurality of identifiers 23 by the evaluation unit 13.

Figure 4:
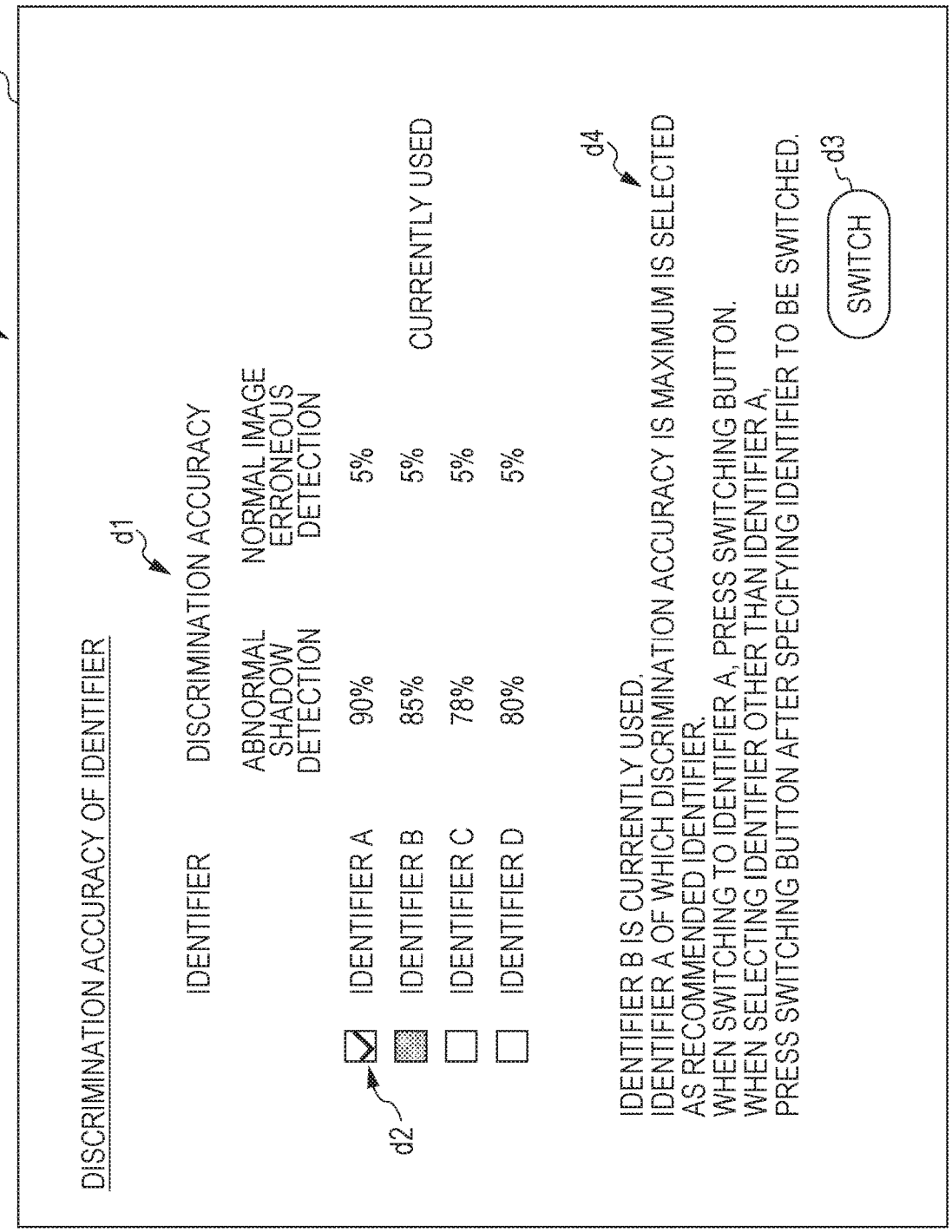
FIG. 4 is a view illustrating an example of a display screen of a display unit.

FIG. 4 is a view illustrating an example of a display screen D of the display unit 34.

In FIG. 4, a result of calculating the detection ratio of the abnormal shadow and the ratio of erroneously recognizing the normal image as including the abnormal shadow for each identifier 23 in a case where there are four identifiers 23 usable at the facility H which are identifiers A23a, B23b, C23c, and D23d is displayed in a discrimination accuracy field d1.

Also, a check box is displayed in a selection field d2, and the check box of the currently used identifier 23 (identifier B23b in FIG. 4) is shaded. Also, the check box of the identifier 23 (identifier A23a in FIG. 4) of which discrimination accuracy by the evaluation unit 13 is the maximum is checked as the identifier 23 recommended by the information processing device 3.

When the user wants to select the identifier 23 other than the identifier A23a, the user checks the selection field d2 beside the identifier 23 which is wanted to be selected and operates a switching button d3.

Meanwhile, in a comment field d4, a comment regarding the current identifier 23, the identifier 23 recommended by the device based on the discrimination accuracy and the like is displayed, and the user may select the identifier 23 with reference to this comment.

When the switching button d3 is operated, an operation signal is output to the control device 30, and the selection unit 14 switches the identifier 23 currently used (identifier B23b in FIG. 4) to the identifier 23 checked in the selection field d2.

Meanwhile, the checking of the check box in the selection field d2 and the input operation to the switching button d3 are performed by the operation unit 33 formed of the keyboard and the like, but in a case where a touch panel is integrally formed on a surface of the display unit 34, it is also possible to perform operation such as selection by directly touching the screen.

Meanwhile, in a case where no operation signal is input from the switching button d3, the selection unit 14 switches the identifier 23 to be used from the identifier 23 currently used (identifier B23b in FIG. 4) to the identifier 23 recommended by the device (identifier A23a in FIG. 4).

The identifier 23 recommended by the device is the identifier highly evaluated by the evaluation unit 13, In a case where there is the identifier 23 with high discrimination accuracy in all evaluation characteristics in each of the detection ratio of the abnormal shadow and the ratio of erroneously recognizing the normal image, the selection unit 14 selects this identifier 23 as the identifier 23 recommended by the device and switches the identifier 23 to be used to this.

In addition, in a case where the discrimination accuracy is different between the detection ratio of the abnormal shadow and the ratio of erroneously recognizing the normal image (for example, although the identifier A23a is more excellent in the detection ratio of the abnormal shadow, the identifier B23b is more excellent in the ratio of erroneously recognizing the normal image and the like), the selection unit 14 may select one having higher discrimination accuracy according to a detection target. In this case, the selection unit 14 switches the identifier 23 to be used according to the detection target so that the identifier 23 having excellent discrimination accuracy is set as the identifier 23 used at the facility H.

It is also possible to set in advance one having priority between the evaluation result regarding the detection ratio of the abnormal shadow and the evaluation result regarding the ratio of erroneously recognizing the normal image, and the selection unit 14 may select the one with an excellent evaluation result with higher priority. In this case, irrespective of the detection target, the selected identifier 23 is set as the identifier 23 to be used at the facility H.

The abnormal shadow detection unit 15 applies the identifier 23 selected by the selection unit 14 to be switched (set)

and detects the abnormal shadow on the medical image data obtained by the modality 5 and stored in the image management server 7.

The display control unit 16 controls the display of the display unit 34 to display the discrimination accuracy for each identifier 23 as illustrated in FIG. 4 and display the medical image for interpretation.

The storage unit 32 stores data and the like necessary for the information processing device 3 to perform various processes. In this embodiment, the storage unit 32 includes various storage areas such as a program storage area 21, an identifier storage area 22 which stores a plurality of identifiers 23, and an evaluation result storage area 24 which stores the evaluation result by the evaluation unit 13.

Meanwhile, a storage area other than that illustrated in FIG. 1 may also be provided in the storage unit 32, or all or a part of the storage areas illustrated in FIG. 1 may be provided outside the storage unit 32.

The program storage area 21 is an area for storing various programs necessary for the control unit 31 to control each unit of the information processing device 3. In this embodiment, for example, a program for the customization unit 12 to customize the evaluation data, a program for the evaluation unit 13 to evaluate the identifier 23, a program for the selection unit to select one identifier 23 from a plurality of identifiers 23 and the like are stored in the program storage area.

The identifier storage area 22 stores a plurality of identifiers 23 such as a general-purpose identifier 23 set in the initial state of the information processing device 3 and the identifier 23 newly generated by subsequent learning (machine learning).

The evaluation result storage area 24 is an area for storing the evaluation result of the discrimination accuracy of each identifier 23 by the evaluation unit 13.

[Action of information Processing Device (Information Processing Method)]

Next, a process executed by the information processing device 3 in this embodiment is described with reference to FIG. 5.

Figure 5:
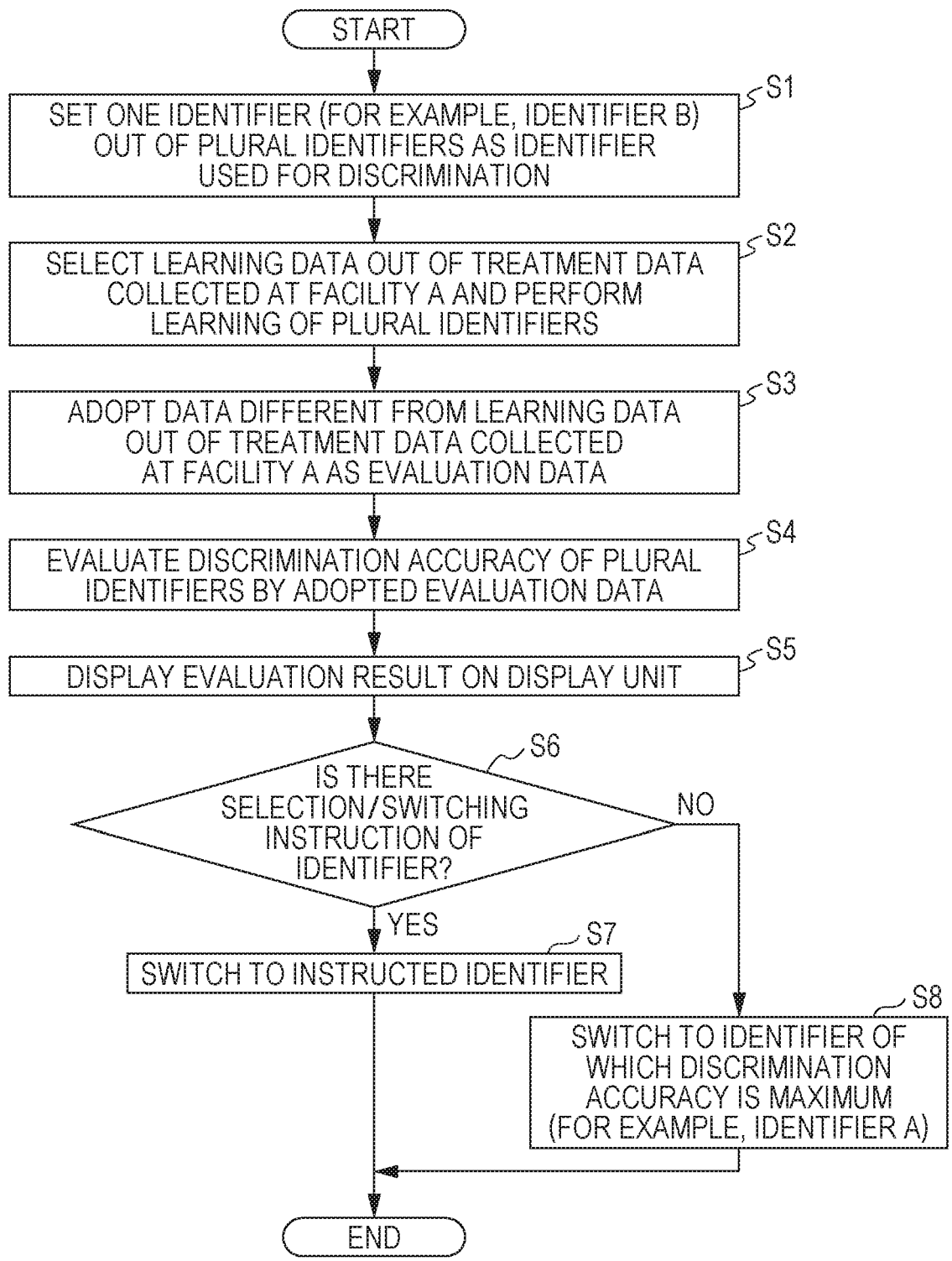
FIG. 5 is a flowchart illustrating an information processing method according to the first embodiment.

As illustrated in FIG. 5, for example, in the information processing device 3 provided in the facility A Ha illustrated in FIG. 1, any one of the identifiers 23 (for example, identifier B23b) is set as the identifier 23 for discriminating the abnormal shadow (step S1).

The identifier generation unit 11 selects the learning data from the treatment data collected at the facility A Ha (treatment data A_a, treatment data A_b, treatment data A_c and the like in FIG. 2) and performs the learning about a plurality of identifiers 23 (step S2) as illustrated in FIG. 2.

Also, the customization unit 12 adopts the treatment data different from that selected as the learning data from the treatment data (treatment data A_a, treatment data A_b, treatment data A_c and the like in FIG. 2) collected at the facility A Ha as the evaluation data (step S3, refer to FIG. 2).

Then, the evaluation unit 13 evaluates the discrimination accuracy of a plurality of identifiers 23 by the evaluation data adopted and customized by the customization unit 12 (step S4).

In this embodiment, the evaluation unit 13 calculates the ratio which the identifier 23 correctly detects the abnormal shadow and the ratio at which this erroneously detects that there is the abnormal shadow in the normal image.

The calculation result (evaluation result) by the evaluation unit 13 is displayed on the display screen D of the display unit 34 as illustrated in FIG. 4 (step S5).

The user confirms this display screen D, and in a case where the user wants to switch the identifier 23 used for discriminating the abnormal shadow to the desired identifier 23, the user checks the checkbox beside the identifier 23 to which the user wants to switch (for example, identifier D23d) ow of the check boxes of the selection field d2, and then the switching button d3 operates.

The selection unit 14 determines whether a selection/switching instruction of the identifier 23 is input (step S6), and when the check box beside any identifier 23 is checked, and then the switching button d3 is operated, the selection unit 14 determines that the selection/switching instruction of the identifier 23 is input (step S6; YES), and switches the identifier currently used (for example, identifier B23b) to the identifier 23 checked by the user (for example, identifier D23d) (step S7).

On the other hand, in a case where there is no input to the selection field d2 or operation of the switching button d3 (step S6; NO), the selection unit 14 selects the identifier evaluated by the evaluation unit 13 to have the maximum discrimination accuracy (for example, identifier A23a) and switches the identifier currently used (for example, identifier B23b) to the identifier 23 (for example, identifier A23a) Which is highly evaluated (step S8).

[Effects of Information Processing Device and Information Processing Method]

In this manner, the treatment data is divided into the learning data and the evaluation data and the learning and evaluation are performed using different data in this embodiment. As a result, it is possible to appropriately evaluate whether the abnormal shadow may be correctly discriminated as for new data that is not learned.

In addition, since the customization unit 12 customizes the evaluation data so that the treatment data collected at the facility (facility A Ha in this embodiment) in which the identifier 23 is used is used as the evaluation data, the evaluation unit 13 may appropriately evaluate the discrimination accuracy for the data according to the characteristic at the facility (facility A Ha) by evaluating the discrimination accuracy of the identifier 23 by using the customized evaluation data.

As described above, according to this embodiment, the customization unit 12 customizes the evaluation data used when the evaluation unit 13 evaluates the discrimination accuracy of a plurality of identifiers 23, and the evaluation unit 13 calculates the discrimination accuracy of each of a plurality of identifiers 23 by using the evaluation data customized by the customization unit 12. Then, based on the calculation result by the evaluation unit 13, the selection unit 14 selects one identifier 23 from a plurality of identifiers 23 as the identifier 23 to be used for discrimination.

This makes it possible to evaluate the discrimination accuracy of the identifier 23 by using the evaluation data according to the characteristic of the facility H in which the identifier 23 is used and minimize discrepancy between the evaluation result and the actual discrimination accuracy as much as possible.

For this reason, it is possible to evaluate a highly reliable identifier 23, and it is possible to discriminate the abnormal shadows and the like at high accuracy by the identifier 23 suitable for the facility H.

Especially, in this embodiment, the customization unit 12 adopts the treatment data collected at the medical institution (for example, facility A Ha) in Which the identifier 23 is used as the evaluation data.

As a result, it is possible to correctly evaluate the discrimination accuracy according to the characteristic of the facility.

In a case where the customization unit 12 adopts the treatment data which the identifier 23 currently used erroneously discriminates as the evaluation data, it is possible to confirm whether the data erroneously discriminated by the identifier 23 before may be correctly discriminated as for the abnormal shadow and whether the discrimination accuracy is improved by repeating the learning when the evaluation unit 13 evaluates.

Furthermore, according to this embodiment, the information processing device 3 is provided with the display unit 34 and the display control unit 16 which controls the same, and the display control unit 16 allows the display unit 34 to display the information of another calculated accuracy when the discrimination accuracy is calculated for a plurality of identifier 23 by the evaluation unit 13.

As a result, the user may confirm the determination accuracy of the identifier 23 by looking at the evaluation result displayed on the display unit 34. Also, when switching the identifier 23 also, it is possible to determine which identifier is to be applied by confirming the evaluation result of the evaluation unit 13, and it is possible to comprehensively and easily select the appropriate identifier.

Second Embodiment

Next, a second embodiment of an information processing device and an information processing method according to the present invention is described with reference to FIGS. 6 and 7. Meanwhile, in this embodiment, since only a method of customizing treatment data by a customization unit is different from that of the first embodiment, a point different from that of the first embodiment is hereinafter especially described.

Figure 6:
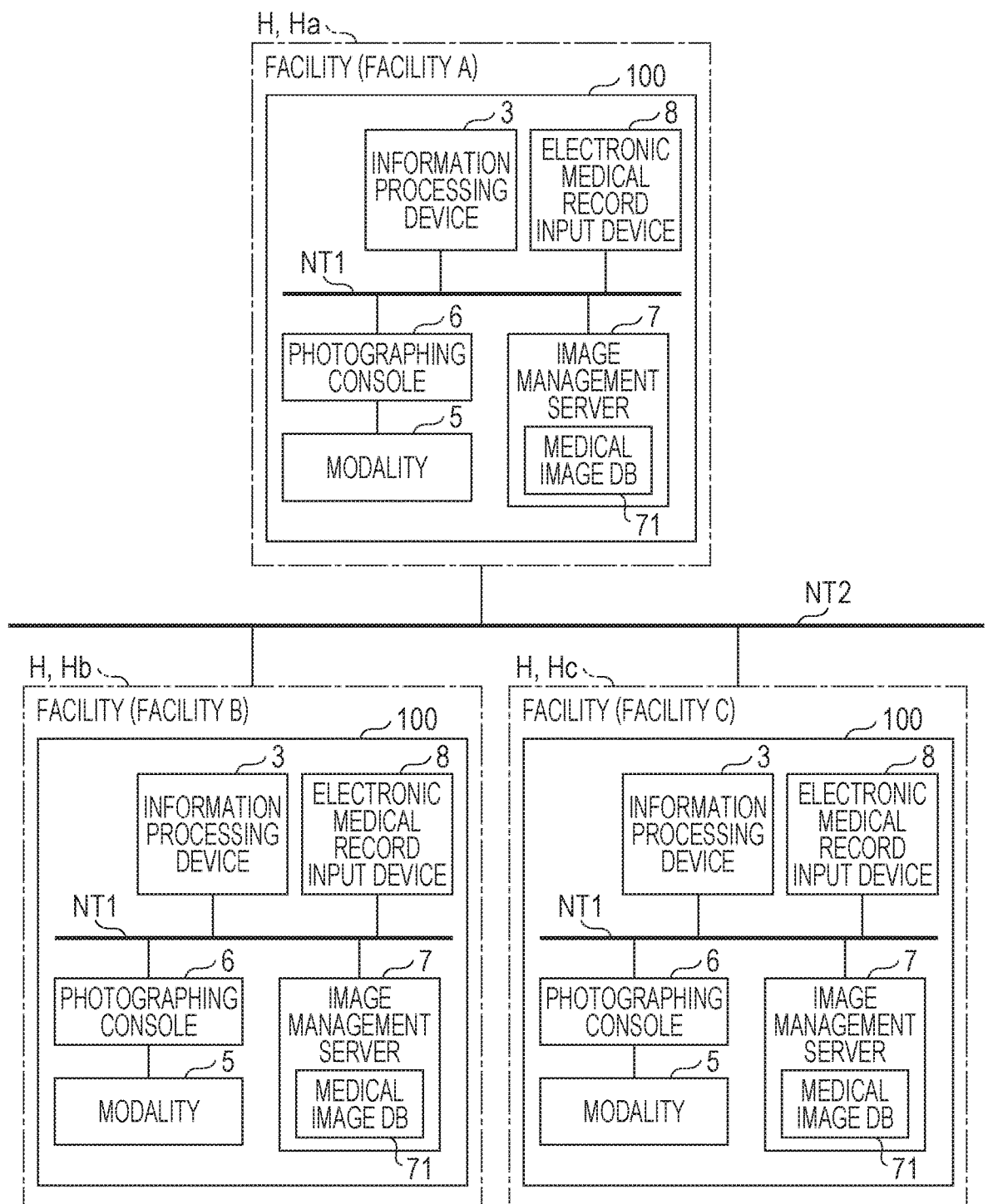
FIG. 6 is a configuration diagram of a substantial part illustrating a system configuration of a medical image system including an information processing device according to a second embodiment.

FIG. 6 is a block diagram illustrating a schematic configuration illustrating a relationship between medical institutions (facilities H) in this embodiment.

As illustrated in FIG. 6, in this embodiment, a plurality of medical institutions (facility A Ha, facility B and facility C Hc in FIG. 6) are configured to be able to transmit and receive information to each other via an external network NT2. Meanwhile, the number of medical institutions connected via the network NT2 is not limited to that illustrated, and more medical institutions may transmit and receive the information mutually.

Figure 7:
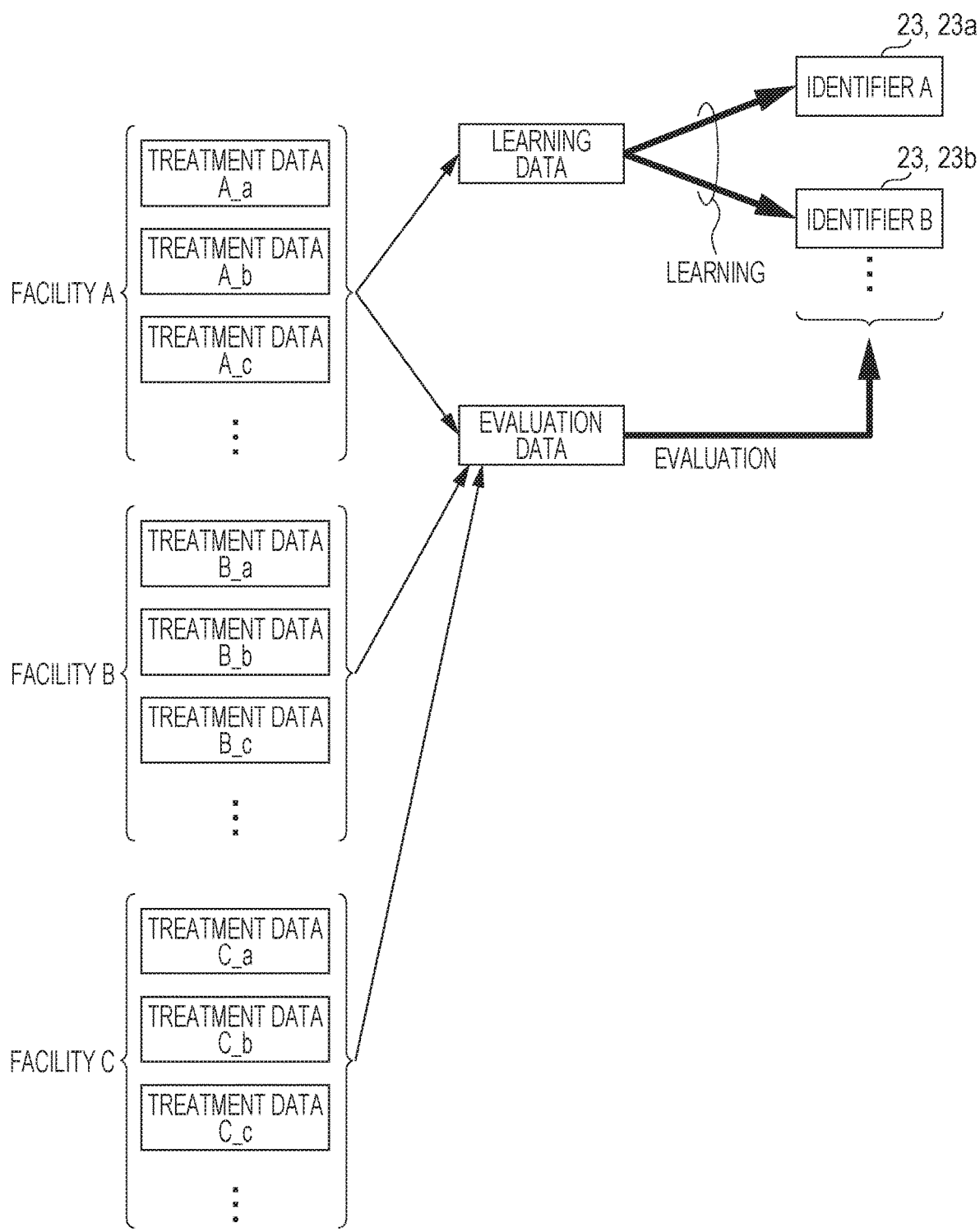
FIG. 7 is an illustrative view schematically illustrating a method of learning and evaluating discrimination accuracy of an identifier in the second embodiment.

FIG. 7 is an illustrative view schematically illustrating a method of learning and evaluating discrimination accuracy of an identifier 23 in this embodiment.

As illustrated in FIG. 7, for example, in a case where treatment data collected at the facility A Ha are treatment data A_a, treatment data A_b, treatment data A_c and the like, treatment data collected at the facility B Hb are treatment data B_a, treatment data B_b, treatment data B_c and the like, and treatment data collected at the facility C Hc are treatment data C_a, treatment data C_b, treatment data C_c and the like, an information processing device 3 of the facility A Ha divides the treatment data into learning data used for learning of the identifier 23 and evaluation data used for evaluating the discrimination accuracy; and the learning (machine learning) of the identifier 23 used in the facility A Ha (identifiers A23*a* and B23*b* in FIG. 7) and the evaluation of the discrimination accuracy are performed by using the data.

Specifically, a customization unit 12 divides the treatment data A_a, treatment data A_b, treatment data A_c and the like collected at the facility A Ha being its own facility H into the learning data and the evaluation data. Also, this adopts the treatment data B_a, treatment data B_b, treatment data B_c and the like collected at the facility B Hb, and the treatment data C_a, treatment data C_b, treatment data C_c and the like collected at the facility C Hc as the evaluation data.

In this manner, at the facility A Ha, by adding the treatment data collected at the facility B Hb and the facility C Hc different from its own facility H as well in the evaluation data, it is possible to make a large amount of treatment data the evaluation data even in a case where the treatment data sufficient for performing appropriate evaluation cannot be collected only at its own facility H.

Meanwhile, the customization unit 12 may adopt all of the treatment data collected at the facility B Hb and the treatment data collected at the facility C Hc as the evaluation data, or may select a part of the treatment data from them randomly or based on a certain criterion to use as the evaluation data.

Also, although an example in which a part of only the treatment data collected at the facility A Ha is made the learning data is illustrated in FIG. 7, the treatment data forming the learning data is not limited to the treatment data collected at the facility A Ha. For example, the customization unit 12 may divide the treatment data collected at the facility B Hb and the treatment data collected at the facility C He into the learning data and evaluation data and adopt a part of the treatment data collected at the facility B Hb and the treatment data collected at the facility C Hc also as the learning data.

Also, the customization unit 12 is not required to make the treatment data of all the facilities H connected via the network NT2 the evaluation data; for example, this may adopt only the treatment data of the facility H having the same characteristic as that of the facility A Ha being its own facility H as the evaluation data. That is, in a case where the facility A Ha is a facility with many elderly patients, the treatment data collected at the facility H in which many elderly patients are treated similarly is adopted as the evaluation data.

In addition, in a case where the facility A Ha being its own facility H is a facility specialized in specific disease, it is possible to select the evaluation data such that discrimination accuracy becomes high for the specific disease; the treatment data of the facility H proven for the disease and the facility H where a doctor with proven past in treating the disease treats is adopted as the evaluation data, the treatment data of a case charged by the doctor having the proven past in treating the disease is surely adopted as the evaluation data and the like.

In addition, the evaluation data may be made common so that the same evaluation data is used in the facilities H belonging to the same group, for example. By making the evaluation data used for evaluating the discrimination accuracy of the identifier 23 common in this manner, it is possible to make an evaluation level of the discrimination accuracy of the identifier 23 uniform among the facilities H.

Also, by using common evaluation data at a plurality of facilities H, it is also possible to estimate a characteristic of each facility H from an evaluation result. For example, in a case where the discrimination accuracy of the identifier 23 is evaluated using the common evaluation data among a plurality of general hospitals, if the evaluation result is low only at a certain facility H, there might be a case where the characteristic becomes obvious such that most of the patients are elderly patients or infants only in this facility H as compared to other facilities H when the cause thereof is analyzed. In this case, by collecting treatment data according to the characteristic of this facility H and adopting the same as the evaluation data, it is possible to make the evaluation of the discrimination accuracy of the identifier 23 to be appropriate according to the characteristic of this facility H.

In addition, it is not always determined by the customization unit 12 of the information processing device 3 of the facility H (for example, the facility A Ha) which receives the treatment data, the treatment data used as the evaluation data from the treatment data collected at each facility H. For example, it is also possible that the facility H which provides the treatment data (for example, facility B Hb and facility C Hc) selects especially reliable treatment data and the like such as that a diagnostic result of which is definite as the treatment data to be adopted as the evaluation data and presents the same to another facility H.

Furthermore, for example, in a case where there is no treatment data of which treatment result (presence or absence of disease or lesion) is definite such as in a case where the facility A Ha being its own facility H is newly opened, the customization unit 12 may adopt, for example, the treatment data collected at another facility H having the common patient characteristic and the like (for example, treatment data Ba, treatment data B_b, treatment data B_c and the like collected at the facility B Hb, and treatment data C_a, treatment data C_b, treatment data C_c and the like collected at the facility C Hc) as the evaluation data without adopting the treatment data A_a, the treatment data A_b, the treatment data A_c and the like of the facility A Ha as the evaluation data.

Meanwhile, the customization unit 12 may automatically determine the facility H the treatment data of which is adopted as the evaluation data, whether all the treatment data of the same facility H is included in the evaluation data, or whether only the one selected from the treatment data randomly or according to a certain condition is adopted as the evaluation data, example, or a human may set and input and the customization unit 12 may determine according to the setting and input.

Meanwhile, since other configurations are similar to those of the first embodiment, the same reference sign is given to the same member, and the description thereof is omitted.

Next, an action (information processing method) of the information processing device in this embodiment is described.

In this embodiment, the customization unit 12 adopts all or a part of the treatment data B_a, treatment data B_b, treatment data B_c and the like collected at the facility B Hb, and the treatment data C_a, treatment data C_b, treatment data C_c and the like collected at the facility C Hc in addition to the treatment data (treatment data A_a, treatment data A_b, treatment data A_c and the like in FIG. 7) collected at the facility A Ha as the evaluation data. In this manner, by customizing such that the treatment data of a plurality of facilities H is made the evaluation data, it is possible to secure a sufficient number of evaluation data even in a case where the number of treatment data is small only in its own facility H.

The evaluation unit 13 evaluates the discrimination accuracy of the identifier 23 using the evaluation data customized by the customization unit.

Meanwhile, since other points are similar to those of the first embodiment, the description thereof is omitted.

As described above, according to this embodiment, in addition to obtaining the effects similar to those of the first embodiment, the following effects may be obtained.

That is, in this embodiment, the customization unit 12 adopts the treatment data collected at one or a plurality of medical institutions (facilities H) which is not the medical institution in which the identifier 23 is used as the evaluation data.

As a result, even in a case where the number of treatment data is small only at its own facility H and it is not possible to secure a sufficient number of evaluation data, it is possible to evaluate the identifier 23 with high reliability using many evaluation data, and it becomes possible to discriminate abnormal shadow and the like with high accuracy by the identifier 23 suitable for the facility H.

Third Embodiment

Next, a third embodiment of an information processing device and an information processing method according to the present invention is described with reference to FIG. 8 to FIG. 10. Meanwhile, in this embodiment, since a method of customizing treatment data by a customization unit and the like is different from that of the first embodiment and the like, a point different from that of the first embodiment and the like is hereinafter especially described.

Figure 8:
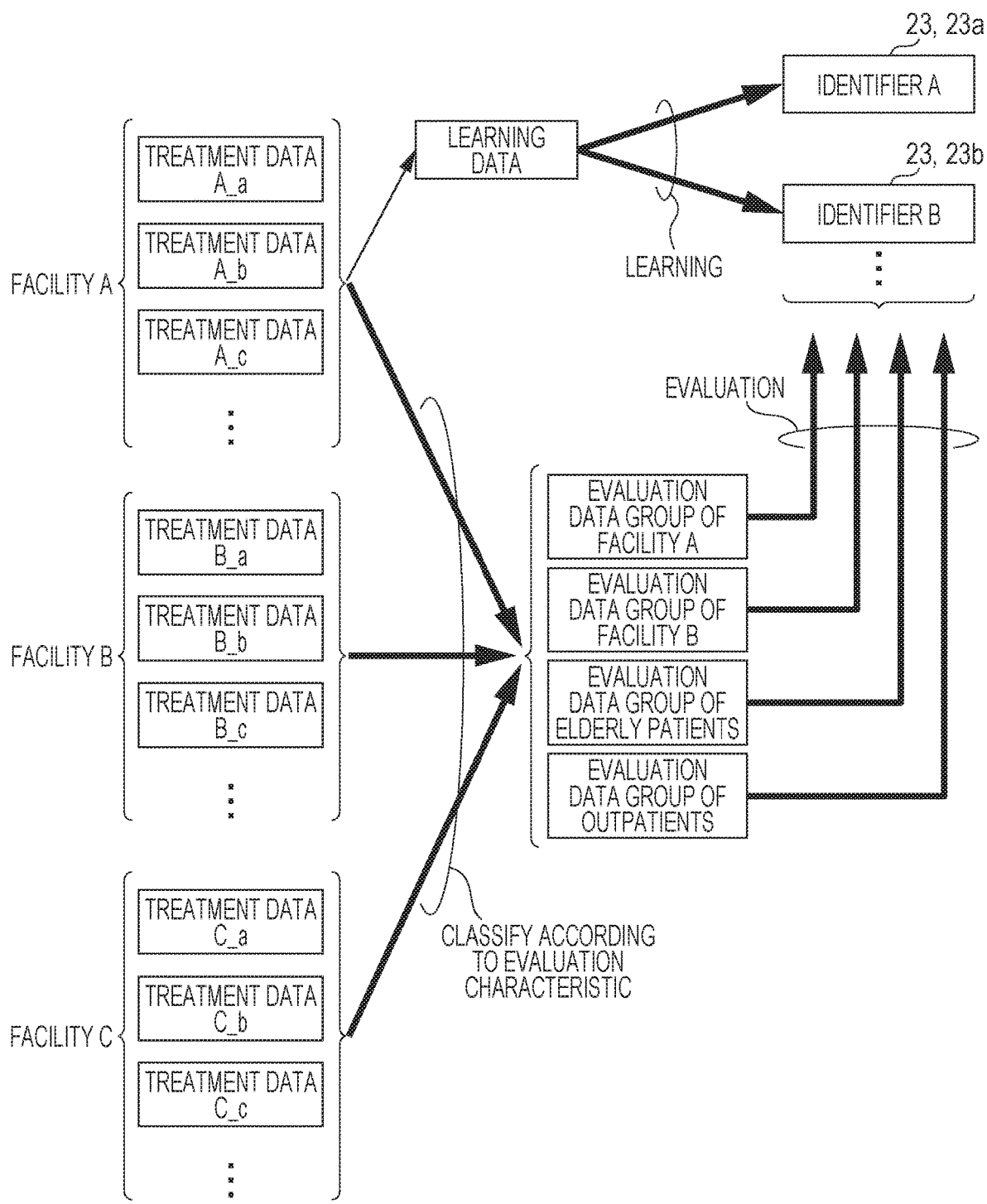
FIG. 8 is an illustrative view schematically illustrating a method of learning and evaluating discrimination accuracy of an identifier in a third embodiment.

FIG. 8 is an illustrative view schematically illustrating a method of learning and evaluating discrimination accuracy of an identifier 23 in this embodiment.

As illustrated in FIG. 8, in this embodiment, a plurality of medical institutions (facility A Ha, facility B Hb, and facility C Hc in FIG. 8) is connected so as to be able to transmit and receive information via an external network NT2 as in the second embodiment. Meanwhile, the number of medical institutions connected via the network NT2 is not limited to that illustrated, and more medical institutions may transmit and receive the information mutually.

As illustrated in FIG. 8, for example, in a case where treatment data collected at the facility A Ha are treatment data A_a, treatment data A_b, treatment data A_c and the like, treatment data collected at the facility B Hb are treatment data B_a, treatment data B_b, treatment data B_c and the like, and treatment data collected at the facility C Hc are treatment data C_a, treatment data C_b, treatment data C_c and the like, an information processing device 3 of the facility A Ha divides the treatment data into learning data used for learning of the identifier 23 and evaluation data used for evaluating discrimination accuracy, and performs the learning machine learning) of the identifier 23 used in the facility A Ha (identifiers A23a and B23b in FIG. 2) and evaluation of the discrimination accuracy by using the data.

Specifically, a customization unit 12 divides the treatment data A_a, treatment data A_b, treatment data A_c and the like collected at the facility A Ha being its own facility H into the learning data and the evaluation data. Also, this adopts the treatment data B_a, treatment data B_b, treatment data B_c and the like collected at the facility B Hb, and the treatment data C_a, treatment data C_b, treatment data C_c and the like collected at the facility C Hc as the evaluation data.

Meanwhile, the customization unit 12 may adopt all of the treatment data collected at the facility B Hb and the treatment data collected at the facility C Hc as the evaluation data, or may select a part of the treatment data from them randomly or based on a certain criterion to use as the evaluation data.

Also, although an example in which a part of only the treatment data collected at the facility A Ha is used as the learning data is illustrated in FIG. 8, the treatment data forming the learning data is not limited to the treatment data collected at the facility A Ha. For example, the customization unit 12 may divide the treatment data collected at the facility B Hb and the treatment data collected at the facility C Hc into the learning data and evaluation data and adopt a part of the treatment data collected at the facility B Hb and the treatment data collected at the facility C He also as the learning data.

Then, the customization unit 12 of this embodiment classifies the treatment data (a plurality of evaluation data) classified as the evaluation data according to an evaluation characteristic thereof, and adopts one or a plurality of evaluation data groups classified to the evaluation characteristic specified according to a situation of the medical institution (for example, facility A Ha) in which the identifier 23 is used as the evaluation data used when evaluating the discrimination accuracy of a plurality of identifiers 23 (identifiers A23a and B23b in FIG. 8).

Herein, the evaluation characteristic is trend/characteristic of characteristic treatment data that influences an evaluation result in evaluating the discrimination accuracy of the identifier 23.

For example, FIG. 8 illustrates an example in which "the treatment data collected at the facility A Ha", "the treatment data collected at the facility B Hb", "the treatment data of elderly patients", and "the treatment data of outpatients" are made the evaluation characteristics, and the customization unit 12 extracts and classifies the data having such evaluation characteristics out of a plurality of evaluation data to customize four evaluation data of different evaluation characteristics of "an evaluation data group formed of the treatment data collected at the facility A Ha", "an evaluation data group formed of the treatment data collected at the facility B Hb", "an evaluation data group formed of the treatment data of elder patients", and "an evaluation data group formed of the treatment data of outpatients".

Meanwhile, the evaluation characteristics when classifying the treatment data are not limited to those illustrated in FIG. 8. For example, as characteristics regarding the patient, in addition to age of the patient, there may be patient's sex, body types of the patient (body height, body weight and the like), a type of affected disease, a past history, resident areas, smoking habits, drinking habits and the like. Also, the treatment data may be classified using various characteristics such as a type of modality used for photographing as the evaluation characteristics.

The customization unit 12 classifies the treatment data based on the evaluation characteristics by extracting the one conforming to a condition set in advance and one exceeding a predetermined threshold by referring to accompanying information of a medical image included in the treatment data and electronic medical record information and the like of the patient associated with the medical image data. Meanwhile, the classification based on the evaluation characteristics is not limited to a case where this is automatically performed by the customization unit 12, but for example, it is also possible that a person selects according to the evaluation characteristics and the customization unit 12 classifies each evaluation data so as to belong to the evaluation data group of each evaluation characteristic according to the selection.

An evaluation unit 13 calculates the discrimination accuracy of each of a plurality of identifiers 23 using one or a plurality of (four in this embodiment) evaluation data (evaluation data groups) customized by the customization unit 12.

In this embodiment, the evaluation unit 13 evaluates the discrimination accuracy for each of a plurality of identifiers 23 (identifiers A23a and B23b in FIG. 8) for each of the evaluation data groups having different evaluation characteristics.

Specifically, it is evaluated for each of the evaluation data groups having different evaluation characteristics in two viewpoints; a ratio at which abnormal shadow may be discriminated and a ratio of erroneously recognizing a normal image as including the abnormal shadow for each identifier 23 and calculates the discrimination accuracy of each of them.

FIG. 9 illustrates a calculation result in a case where the detection ratio of the abnormal shadow and the ratio of erroneously recognizing the normal image are calculated for each identifier 23.

In the result illustrated in FIG. 9, there is no difference in ratio of erroneously recognizing the normal image in any evaluation characteristic between the identifiers A23a and B23b (5%), but as for the detection ratio of the abnormal shadow, this is 90% when "the treatment data group collected at the facility A Ha" is made the evaluation data, 80% when "the treatment data group collected at the facility A Ha" is made the evaluation data, 99% when "the treatment data group of the elderly patients" is made the evaluation data, and 95% when "the treatment data group of the outpatients" is made the evaluation data in the identifier A23a, for example, so that the discrimination accuracy of the identifier A23a is the highest when "the treatment data group of the elderly patients" is made the evaluation data.

Also, in the identifier B23b, this is 85% when "the treatment data group collected at the facility A Ha" is made the evaluation data, 95% when "the treatment data group collected at the facility B Hb" is made the evaluation data, 75% when "the treatment data group of the elderly patients" is made the evaluation data, and 85% when "the treatment data group of the outpatients" is made the evaluation data in the identifier B23b, so that the discrimination accuracy is the highest when "the treatment data group collected at the facility B Hb" is made the evaluation data.

Meanwhile, the evaluation unit 13 may individually apply the four evaluation data groups customized by the customization unit 12 and evaluate the identifier 23, or apply a combination of a plurality of evaluation data groups among them to evaluate the identifier 23.

For example, it is possible that "the treatment data group collected at the facility A Ha" and "the treatment data group of the elderly patients" are combined to be made the evaluation data, and the evaluation unit 13 evaluates the discrimination accuracy regarding the evaluation data being the treatment data collected at the facility A Ha and the treatment data of the elderly patients.

As a result, it becomes possible to calculate the evaluation result according to the characteristic of the facility H.

A selection unit 14 selects one identifier 23 out of a plurality of identifiers 23 (identifier A23a and identifier B23b in FIG. 2) as the identifier 23 used to discriminate whether there is abnormal data (abnormal shadow) on the basis of the calculation result by the evaluation unit 13.

In this embodiment, when the user selects and inputs the identifier 23 which is wanted to be used at the facility H by operating the operation unit 33 and the like based on the calculation result by the evaluation unit 13, and the selection/input result is output to the control device 30, the selection unit 14 selects to set the identifier 23 selected by the user as the one to be used for discriminating the presence or absence of the abnormal data (abnormal shadow) in response to the selection result. That is, in a case where the one other than the identifier 23 currently used at the facility H is selected, the identifier 23 is switched to the selected one.

When there is no particular selection/input operation by the user, the selection unit 14 switches the identifier 23 to be used from the currently used identifier 23 (for example, identifier B23b) to the identifier 23 having the highest evaluation by the evaluation unit 13.

Meanwhile, in a case Where there is the identifier 23 with high discrimination accuracy in all the evaluation characteristics in each of the detection ratio of the abnormal shadow and the ratio of erroneously recognizing the normal image, the selection unit 14 selects this identifier 23 and switches the identifier 23 to be used to this.

In addition, in a case where the discrimination accuracy is different between the detection ratio of the abnormal shadow and the ratio of erroneously recognizing the normal image (for example, although the identifier A23a is more excellent in the detection ratio of the abnormal shadow, the identifier B23b is more excellent in the ratio of erroneously recognizing the normal image and the like), the selection unit 14 may select one having higher discrimination accuracy according to a detection target. In this case, the selection unit 14 switches the identifier 23 to be used according to the detection target so that the identifier 23 having excellent discrimination accuracy is set as the identifier 23 used at the facility H.

It is also possible to set in advance one having priority between the evaluation result regarding the detection ratio of the abnormal shadow and the evaluation result regarding the ratio of erroneously recognizing the normal image, and the selection unit 14 may select the one with an excellent evaluation result with higher priority. In this case, irrespective of the detection target, the selected identifier 23 is set as the identifier 23 to be used at the facility H.

Also, in a case where the discrimination accuracy differs for each evaluation characteristic of the evaluation data (for example, the identifier A23a is more excellent in the evaluation using the evaluation data of the elderly patients, but the identifier B23b is more excellent in the evaluation using the evaluation data of the outpatients), the selection unit 14 may select the one with higher discrimination accuracy according to the characteristic of its own facility H (for example, facility A Ha) and the characteristic of the patient corresponding to the medical image to be discriminated by applying the identifier 23. For example, in a case of selecting the one with high discrimination accuracy according to the characteristic of the facility H, the selection unit 14 selects to set the identifier 23 according to the characteristic of its own facility H (for example, facility A Ha) such as to select the identifier 23 excellent in discrimination accuracy in the evaluation using the evaluation data of the elderly patients as the identifier 23 used in the facility H when its own facility H (for example, facility A Ha) is the facility in which there are many elderly patients. In this case, it may be assumed that the set identifier 23 is maintained until there is a change in circumstances such as a change in characteristic of the facility H (the users of the facility H change from the elderly patients to young patients), for example.

In addition, for example, in a case of selecting the one with high discrimination accuracy according to the characteristic of the patient corresponding to the medical image to be discriminated, the selection unit 14 switches the identifier 23 to be used according to the information accompanying the medical image to be discriminated (for example, the age and sex of the patient).

It is also possible to set in advance the evaluation characteristic to be prioritized, and the selection unit 14 selects the one with an excellent evaluation result in the evaluation characteristic with the higher priority. In this case, irrespective of an individual characteristic of the facility H and the like, the selected identifier 23 is set as the identifier 23 to be used at the facility H.

Meanwhile, since other configurations are similar to those of the first embodiment and the like, the same reference sign is given to the same member, and the description thereof is omitted.

Next, an action (information processing method) of the information processing device in this embodiment is described with reference to FIG. 10.

Figure 10:
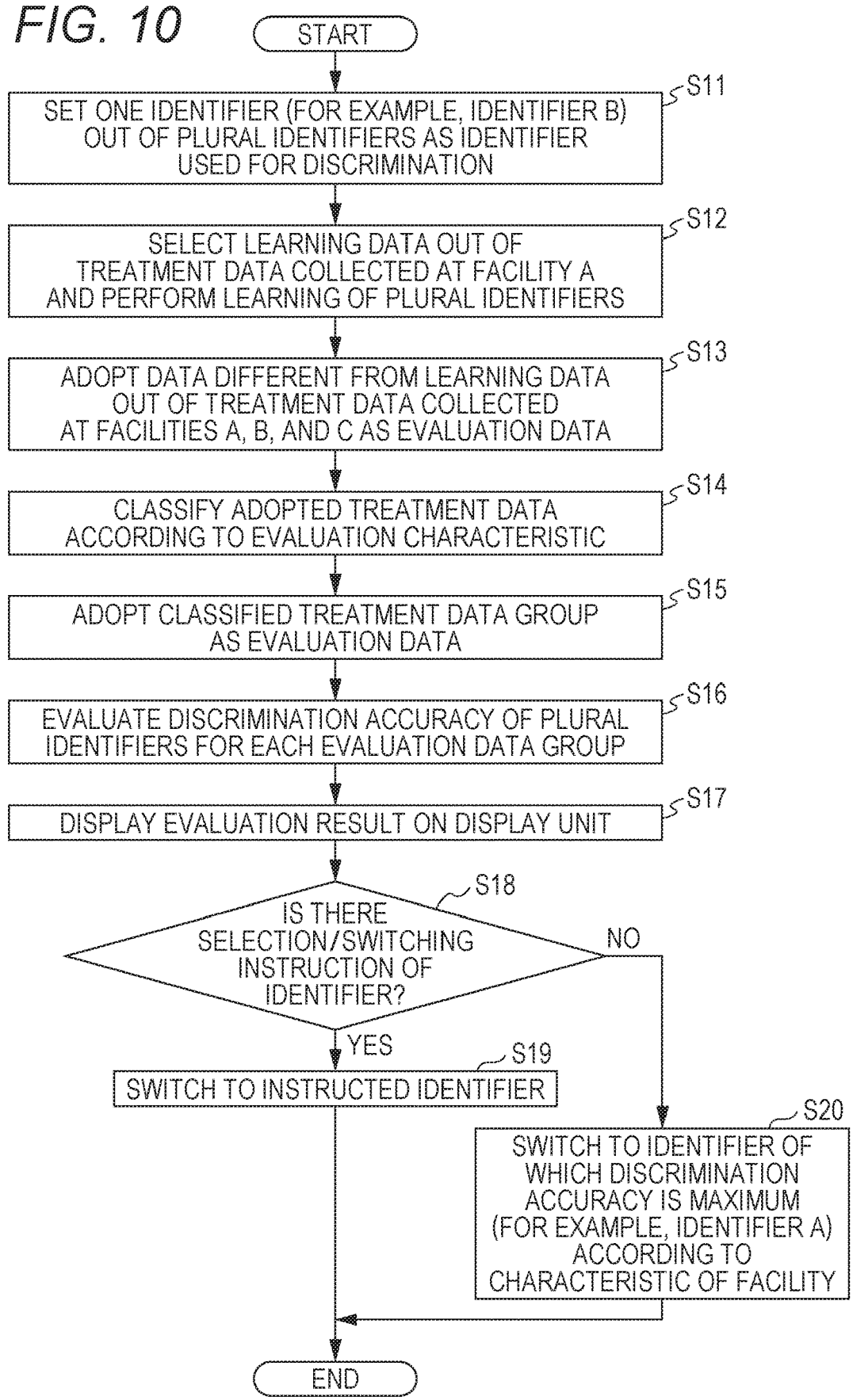
FIG. 10 is a flowchart illustrating an information processing method according to the third embodiment.

Meanwhile, steps S11 and S12 in FIG. 10 are the same as steps S1 and S2 in FIG. 5, and steps S17 to S19 in FIG. 10 are the same as steps S5 to S7 in FIG. 5, so that the description thereof is omitted.

In this embodiment, the customization unit 12 adopts the treatment data different from that selected as the learning data from the treatment data collected at the facility A Ha, the facility B Hb, and the facility C Hc as the evaluation data (step S13).

Furthermore, the customization unit 12 classifies the adopted evaluation data according to the evaluation characteristic (step S14). Meanwhile, the customization unit 12 refers to the accompanying information of the medical image, the electronic medical record information and the like included in the treatment data as information serving as a criterion of classification.

Then, each classified evaluation data group is adopted as the evaluation data for evaluating the discrimination accuracy of the identifier 23 (step S15). In this embodiment, as illustrated in FIG. 8, four evaluation data groups of "the evaluation data group of the facility A Ha", "the evaluation data group of the facility B Hb", "the evaluation data group of the elderly patients" and "the evaluation data group of the outpatients" are customized by the customization unit 12.

The evaluation unit 13 evaluates the discrimination accuracy of each of a plurality of identifiers 23 for each evaluation data (evaluation data group) classified and customized for each evaluation characteristic by the customization unit 12 (step S16).

In this embodiment, the evaluation unit 13 calculates the ratio at which the identifier 23 correctly detects the abnormal shadow and the ratio of erroneously detecting that there is the abnormal shadow in the normal image for each evaluation data (evaluation data group) classified for each evaluation characteristic.

On the basis of the evaluation result by the evaluation unit 13, in a case where the user inputs a selection and switching instruction of the identifier 23, the selection unit 14 selects and switches the identifier 23 according to the instruction (steps S18 and S19). On the other hand, in a case where there is no particular instruction by the user (step S18; NO), the selection unit 14 selects the identifier 23 evaluated by the evaluation unit 13 to have the maximum discrimination accuracy according to the characteristic of the facility H and the like (for example, identifier A23a) and switches the identifier 23 currently used (for example, identifier B23b) to the identifier 23 (for example, identifier A23a) (step S20).

As a result, the optimum identifier 23 reflecting the characteristics of the facility H is set as the identifier 23 used at the facility H.

Meanwhile, since other points are similar to those of the first embodiment and the like, the description thereof is omitted.

As described above, according to this embodiment, in addition obtaining the effect similar to that of the first embodiment and the like, the following effects may be obtained.

That is, in this embodiment, the customization unit 12 classifies a plurality of evaluation data according to the evaluation characteristic, and adopts one or a plurality of evaluation data groups classified to the evaluation characteristic specified according to the situation of the facility H being the medical institution in which the identifier 23 is used as the evaluation data used when evaluating the discrimination accuracy of a plurality of identifiers 23.

In this manner, since the discrimination accuracy of each identifier 23 may be evaluated using the evaluation data according to the situation/characteristic of the facility H, it is possible to appropriately evaluate whether the identifier 23 to be used at each facility H has the discrimination accuracy matching the characteristic of the facility H.

As a result, the identifier 23 matching the characteristic of the facility H may be selected as the identifier 23 used in the facility, and it is possible to highly accurately discriminate the abnormal shadow and the like at the facility H.

Fourth Embodiment

Next, a fourth embodiment of an information processing device and an information processing method according to the present invention is described with reference to FIG. 11 to FIG. 14. Meanwhile, in this embodiment, since only a method of forming learning data is different from that of the first embodiment and the like, a different point from the first embodiment and the like is hereinafter especially described.

Figure 11:
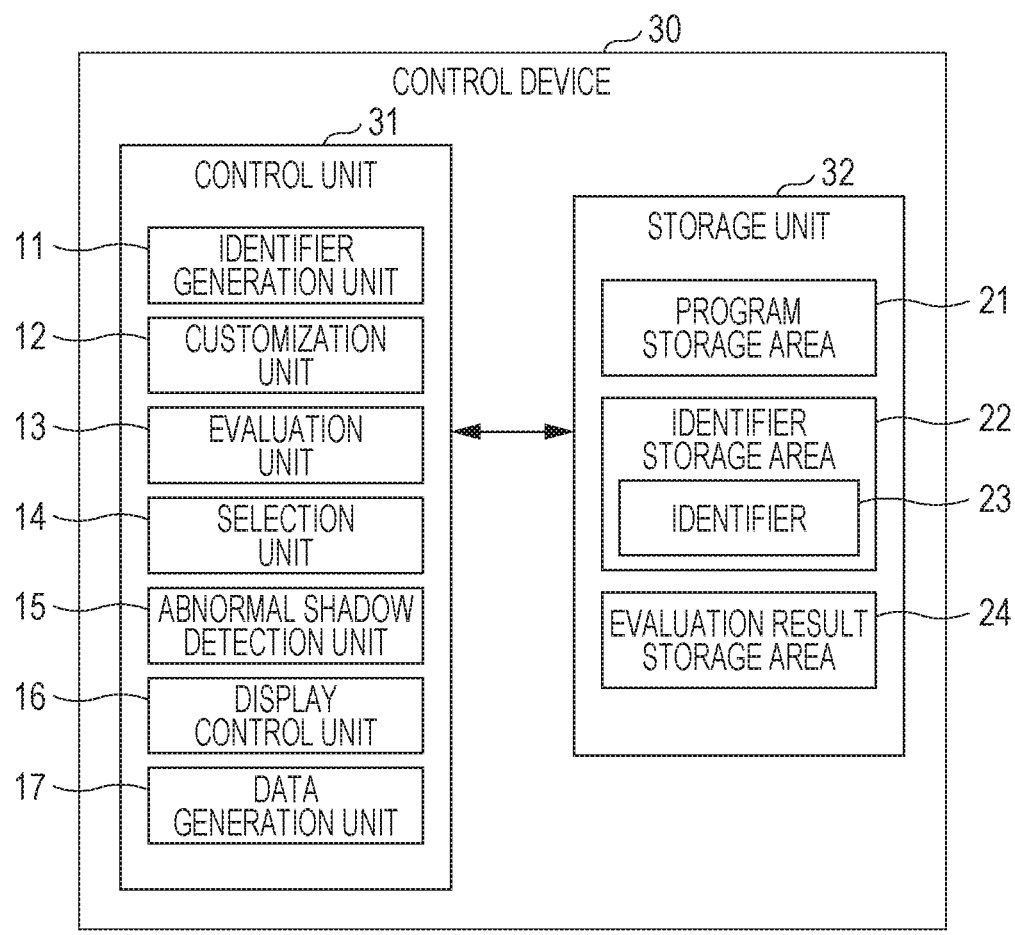
FIG. 11 is a configuration diagram of a substantial part illustrating a configuration of a control device of an information processing device according to a fourth embodiment.

FIG. 11 is a block diagram illustrating a schematic configuration of a control device of the information processing device in this embodiment.

As illustrated in FIG. 11, in this embodiment, a control unit 31 of a control device 30 of an information processing device 3 includes a data generation unit 17.

Figure 12:
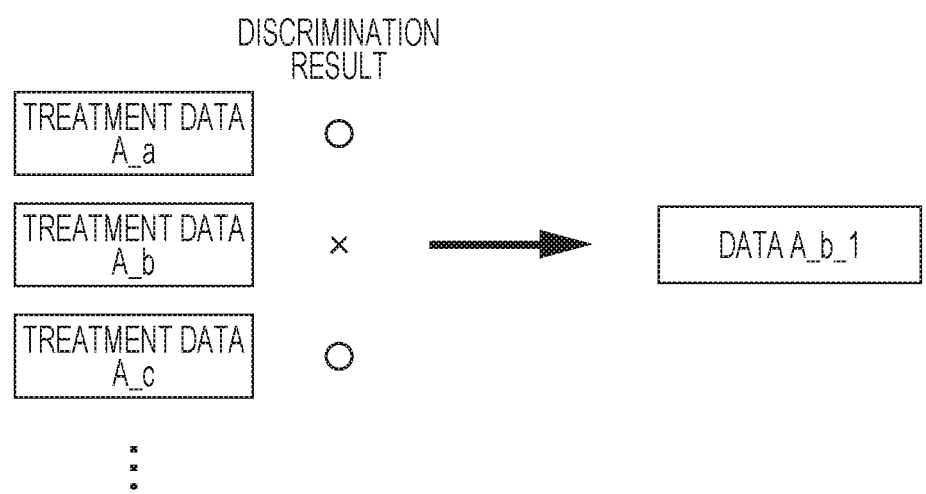
FIG. 12 is an illustrative view illustrating generation of data in the fourth embodiment.

As illustrated in FIG. 12, the data generation unit 17 is a data generator which generates different data (data A_b_1 in FIG. 12) common in characteristic to treatment data (treatment data A_b) in a case where there is the treatment data (data A_b in FIG. 12) in which an identifier 23 currently used erroneously discriminates presence/absence of abnormal shadow.

In this embodiment, the data generation unit 17 generates an image by deep learning on the basis of given original image data, and outputs a different image common in characteristic to the original image data. The data generation unit 17 is formed of an image data generator such as GAN (deep convolutional generative adversarial networks (DC-GAN)), for example. Meanwhile, the data generation unit 17 is not limited to that formed of the GAN, and may also be formed of another image data generator.

Figure 13:
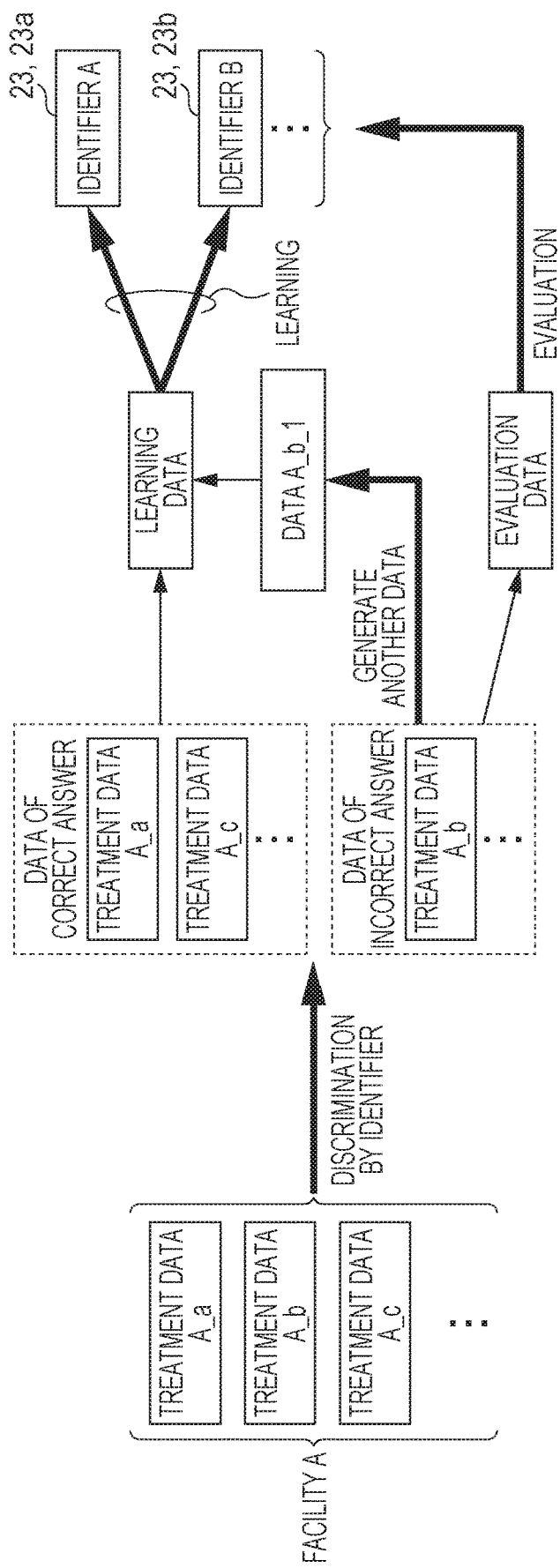
FIG. 13 is an illustrative view schematically illustrating a method of learning and evaluating discrimination accuracy of an identifier in the fourth embodiment.

FIG. 13 is an illustrative view schematically illustrating a method of learning and evaluating discrimination accuracy of the identifier 23 in this embodiment.

As illustrated in FIG. 13, in this embodiment, the customization unit 12 adopts the treatment data (treatment data A_b in FIG. 12) erroneously discriminated by the identifier 23 as evaluation data.

Different treatment data should be used as learning data and the evaluation data, and that adopted as the evaluation data cannot be used as the learning data. However, since the number of treatment data erroneously discriminated by the identifier 23 is generally not so large, if the treatment data erroneously discriminated by the identifier 23 is adopted as the evaluation data, there is a possibility that a case erroneously discriminated by the identifier 23 is not reflected in the learning data.

In this regard, in this embodiment, the identifier generation unit 11 performs the learning of the identifier 23 using data (data Ab_b_1 in FIG. 12) generated by the data generation unit 17 as the learning data, thereby updating a plurality of identifiers 23.

As a result, even in a case where the treatment data erroneously discriminated by the identifier 23 is adopted as the evaluation data and is not included in the learning data, it is possible to perform the learning (machine learning) of data equivalent to the treatment data, and the identifier 23 repeats learning, so that it is updated such that it is possible to correctly discriminate in a case where the treatment data equivalent to that erroneously discriminated in the past is given.

Meanwhile, since other configurations are similar to those of the first embodiment and the like, the same reference sign is given to the same member, and the description thereof is omitted.

Next, an action (information processing method) of the information processing device in this embodiment is described with reference to FIG. 14.

Figure 14:
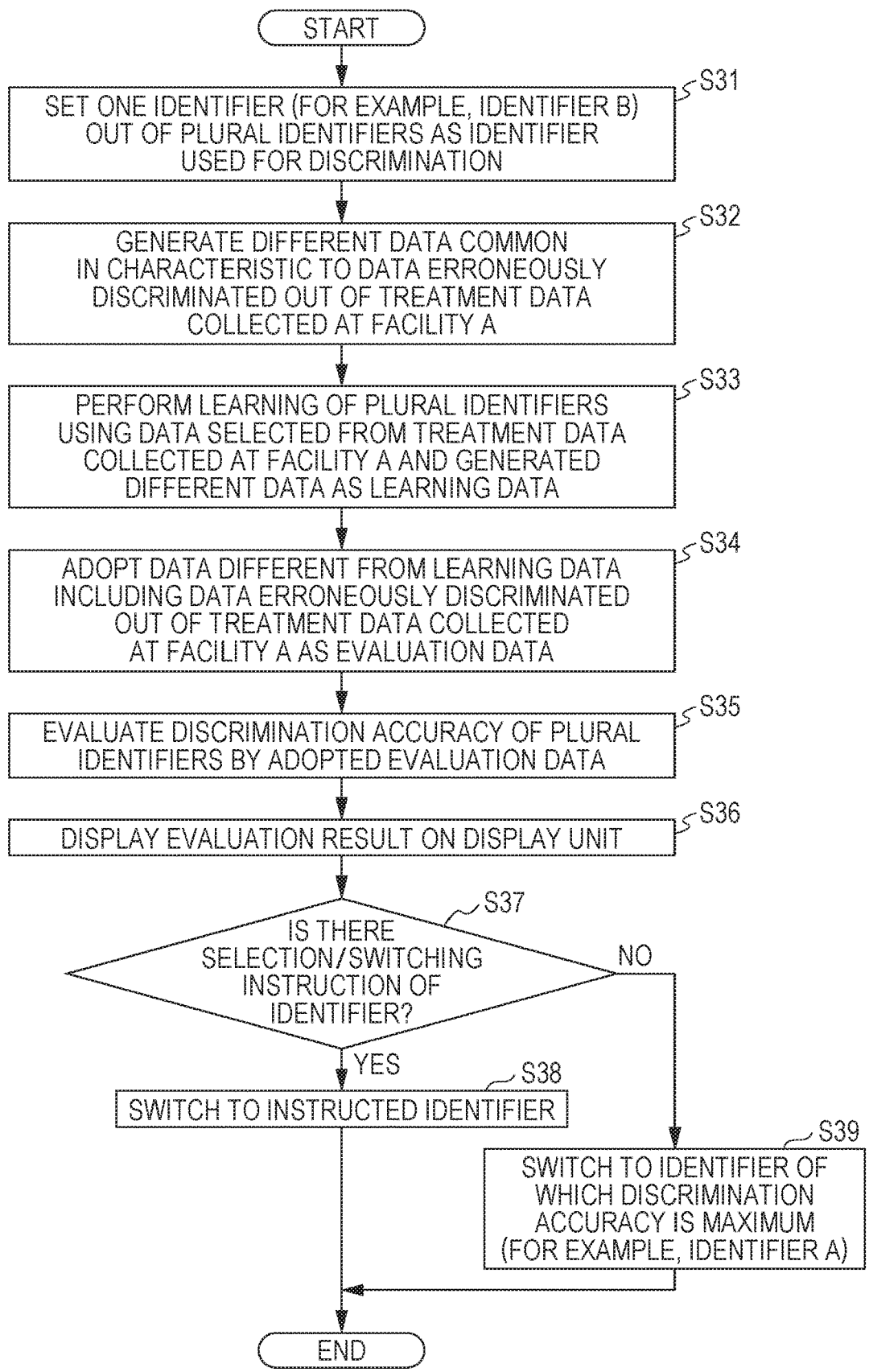
FIG. 14 is a flowchart illustrating an information processing method according to the fourth embodiment.

Meanwhile, step S31 in FIG. 14 is the same as step S1 in FIG. 5, and steps S35 to S39 in FIG. 14 are the same as steps S4 to S5 in FIG. 5, so that the description thereof is omitted.

In this embodiment, as for the treatment data erroneously discriminated by the identifier 23 whether to include the abnormal shadow (treatment data A_b in FIGS. 12 and 13) out of the treatment data collected at the facility A Ha (treatment data A_a, treatment data A_b, treatment data A_c and the like in FIGS. 12 and 13), the data generation unit 17 generates different data (data A_b_1 in FIGS. 12 and 13) common in characteristic to the treatment data (treatment data A_b and original image data) (step S32). Meanwhile, the number of data generated from the original image data by the data generation unit 17 is not limited to one. A plurality of data may also be generated from one treatment data A_b (original image data).

The control unit 31 of the information processing device 3 performs the learning of a plurality of identifiers 23 (step S33) by using the treatment data selected from the treatment data collected at the facility A Ha (for example, treatment data A_a, treatment data A_c and the like in FIG. 12 and FIG. 13) and the generated different data (data A_b_1 in FIG. 12 and FIG. 13) as the learning data.

Also, the customization unit 12 adopts as the evaluation data the data different from the learning data including the treatment data (treatment data A_b in FIGS. 12 and 13) erroneously discriminated by the identifier 23 whether the abnormal shadow is included among the treatment data collected at the facility A Ha (treatment data A_a, treatment data A_b, treatment data A_c and the like in FIGS. 12 and 13) as the evaluation data (step S34).

Then, the evaluation unit 13 evaluates the discrimination accuracy of the identifier 23 using the evaluation data customized by the customization unit 12 (step S35).

As a result, even in a case where the treatment data erroneously discriminated whether to include the abnormal shadow by the identifier 23 is adopted as the evaluation data, it is possible to include data equivalent to this in the learning data, and allows the identifier 23 to perform the learning.

Meanwhile, since other points are similar to those of the first embodiment and the like, the description thereof is omitted.

As described above, according to this embodiment, in addition to obtaining the effect similar to that of the first embodiment and the like, the following effects may be obtained.

That is, in this embodiment, in a case where there is the treatment data (for example, treatment data A_b) erroneously discriminated by the identifier 23 currently used in the facility H, different data (the example, data A_b_1) common in characteristic to this is generated by the data generation unit 17, and the identifier 23 is updated by including the data in the learning data and allowing the identifier 23 to perform the learning.

As a result, even in a case where the customization unit 12 adopts the treatment data (treatment data A_b in FIG. 12) erroneously discriminated by the identifier 23 as the evaluation data, it is possible to perform the learning of the identifier 23 using the data equivalent to this as the learning data.

Therefore, it is possible to allow the identifier 23 to learn the case erroneously discriminated by the identifier 23 and it is also possible to evaluate the discrimination accuracy using the treatment data erroneously discriminated as the evaluation data, and it is possible to appropriately confirm whether the identifier 23 may correctly discriminate the case erroneously discriminated in the past.

Meanwhile, although the embodiments of the present invention are described above, it goes without saying that the present invention is not limited to the embodiments, and various modifications may be made without departing from the gist thereof.

For example, in each of the above-described embodiments, the case where the treatment data is the data of the medical image and the abnormal data which should be discriminated by the identifier 23 is the abnormal shadow appearing in the image is illustrated as an example, but the treatment data is not limited to the image data.

For example, the treatment data may be data of various sounds obtained by auscultation and the like (for example, cardiac sound and cardiac murmur, carotid bruit, respiratory sound and the like obtained by chest auscultation, abdominal bruit and rumbling noise and the like obtained by abdominal auscultation, or may be various waveform data (for example, time-series information of a waveform of an electrocardiogram and the like). Furthermore, the treatment data may be character data such as electronic medical record information, treatment information input by a doctor and the like.

In a case where the treatment data is the sound data, the abnormal data is abnormal sound included in the sound data, for example, and in a case where the treatment data is the waveform data, the abnormal data is an abnormal waveform included in the waveform data, for example, and in a case where the treatment data is character data, the abnormal data is a specific character string and the like (for example, disease name and the like) representing an abnormal situation, for example.

In addition, in a case where the treatment data is data other than the medical image data in this manner as the data generation unit 17 in the fourth embodiment described above, not a unit which generates the image data such as the GAN, but a unit which automatically generates the data corresponding to the treatment data such as the sound data, waveform data, and character data is applied.

Also, the treatment data is not limited to the medical image photographed by a medical image photographing device, and the present invention may also be applied to a case where the identifier performs the discrimination on the image in general.

Also, in the fourth embodiment described above, the case where, when there is the treatment data (for example, treatment data Ab) erroneously discriminated by the identifier 23, the data generation unit 17 formed of the GAN and the like generates the different data (for example, data A_b_1) common in characteristic to the same and the data is included in the learning data is illustrated as an example, the data generation unit 17 formed of the GAN and the like is not limited to that generates from the treatment data erroneously discriminated by the identifier 23 the data similar to this.

For example, in a case where it is desired to form the learning data only by the treatment data of its own facility H, but the number of data is too small to use for the learning of the identifier 23, the data generation unit 17 formed of the GAN and the like may generate a plurality of data similar to existing treatment data to form the learning data. As for the evaluation data also, it is possible to increase the number of data by generating a plurality of data similar to the existing treatment data by the data generation unit 17 formed of the GAN and the like, and use the generated data as the evaluation data.

As a result, even in a case where the number of data suitable for use in the learning or the evaluation of the identifier 23 is insufficient, by compensating the deficiency with the automatically generated data, it becomes possible to perform learning of the identifier 23 or evaluation of the discrimination accuracy appropriately.

In each of the above-described embodiments, the case where the image management server 7 provided with the medical image DB 71 and the like which stores the medical image data and the like is provided in the medical image system 100 in the facility H is described as an example, but the medical image DB 71 and the image management server 7 and the like provided with the same may also be provided on a server device and the like outside the facility H connected so as to be able to transmit and receive information by the network NT2 (refer to FIG. 6) and the like.

When the medical image DB 71 in which a large amount of data is stored, the image management server 7 provided with the same and the like are provided separately from the medical image system 100 in the facility H, the burden on the medical image system 100 may be reduced.

Although embodiments of the present invention have been described and illustrated in detail, the disclosed embodiments are made for purposes of illustration and example only and not limitation. The scope of the present invention should be interpreted by terms of the appended claims.

What is claimed is:

1. An information processing device comprising:
a plurality of identifiers that discriminates whether abnormal data that is information indicating an abnormal value is included in treatment data and detects the abnormal data; and
a hardware processor that:
customizes evaluation data used when evaluating discrimination accuracy of the plurality of identifiers;
calculates the discrimination accuracy of each of the plurality of identifiers using the evaluation data customized by the hardware processor; and
selects one identifier out of the plurality of identifiers as an identifier used for discrimination based on a calculation result by the hardware processor,
wherein the hardware processor customizes the evaluation data by grouping the evaluation data into a plurality of evaluation data groups each having an evaluation characteristic common to the evaluation data included in that evaluation data group, wherein each evaluation data group has a different evaluation characteristic, wherein the hardware processor calculates the discrimination accuracy of each of the plurality of identifiers using the evaluation data of one or a plurality of the evaluation data groups.

2. The information processing device according to claim 1, wherein the hardware processor adopts the treatment data collected at a medical institution in which the identifier is used as the evaluation data.

3. The information processing device according to claim 1, wherein the hardware processor adopts the treatment data collected at one or a plurality of medical institutions which is not a medical institution in which the identifier is used as the evaluation data.

4. The information processing device according to claim 1, wherein the hardware processor adopts the treatment data erroneously discriminated by a currently used identifier as the evaluation data.

5. The information processing device according to claim 1, wherein the hardware processor adopts said one or a plurality of evaluation data groups classified to the evaluation characteristic specified according to a situation of a medical institution in which the identifier is used as the evaluation data used when evaluating the discrimination accuracy of the plurality of identifiers.

6. The information processing device according to claim 1, further comprising:

a data generator that generates different data common in characteristic to the treatment data erroneously discriminated by a currently used identifier, wherein the plurality of identifiers is updated by learning the data generated by the data generator as learning data.

7. The information processing device according to claim 1, further comprising:

a display, wherein the hardware processor controls the display, and allows the display to display information on the discrimination accuracy calculated for the plurality of identifiers.

8. An information processing method comprising:

selecting one identifier out of a plurality of identifiers;

detecting abnormal data by discriminating whether the abnormal data which is information indicating an abnormal value is included in treatment data by using the identifier selected in the selecting;

customizing evaluation data used when evaluating discrimination accuracy of the identifiers; and evaluating to calculate the discrimination accuracy of each of the plurality of identifiers by using the evaluation data customized in the customizing;

wherein, in the selecting, one identifier is selected out of the plurality of identifiers as an identifier used for discrimination based on a calculation result in the evaluating to appropriately switch the identifier, wherein the evaluation data is customized by grouping the evaluation data into a plurality of evaluation data groups each having an evaluation characteristic common to the evaluation data included in that evaluation data group, wherein each evaluation data group has a different evaluation characteristic, wherein the discrimination accuracy of each of the plurality of identifiers is calculated using the evaluation data of one or a plurality of the evaluation data groups.

* * * * *